US012595222B2

(12) United States Patent
Stepanova

(10) Patent No.: US 12,595,222 B2

(45) Date of Patent: Apr. 7, 2026

(54) CURCUMINOIDS, ANALOGS THEREOF, AND METHODS OF MAKING THE SAME

(71) Applicant: WiSys Technology Foundation, Inc., Madison, WI (US)

(72) Inventor: Valeria A. Stepanova, Winona, MN (US)

(73) Assignee: WiSys Technology Foundation, Inc., Madison, WI (US)

(*) Notice: Subject to any disclaimer, the term of this patent is extended or adjusted under 35 U.S.C. 154(b) by 332 days.

(21) Appl. No.: 17/865,037

(22) Filed: Jul. 14, 2022

(65) Prior Publication Data

US 2023/0035796 A1 Feb. 2, 2023

Related U.S. Application Data

(60) Provisional application No. 63/221,768, filed on Jul. 14, 2021.

(51) Int. Cl.

| | |
|---|---|
| ***C07C 45/72*** | (2006.01) |
| ***A01N 35/02*** | (2006.01) |
| ***A01P 1/00*** | (2006.01) |
| ***C07C 49/255*** | (2006.01) |

(52) U.S. Cl.

CPC ............ *C07C 49/255* (2013.01); *A01N 35/02* (2013.01); *A01P 1/00* (2021.08); *C07C 45/72* (2013.01)

(58) Field of Classification Search

CPC ........ C07C 45/72; C07C 49/255; A01N 35/02

See application file for complete search history.

(56) References Cited

U.S. PATENT DOCUMENTS

| | | | | |
|---|---|---|---|---|
| 8,962,674 B2 * | 2/2015 | Takahashi | ............... | A61P 43/00 548/494 |
| 2018/0272013 A1 * | 9/2018 | Spath | ..................... | A01N 55/08 |

OTHER PUBLICATIONS

Samula et al. Synthesis of New Substituted Cycloalkanones. Polish Journal of Chemistry, vol. 59 (1), 73-77. (Year: 1985).*

Guerrero, Andres, et al., "Hybrid Synthetic-Computational Study Of Versatile Approach to Curcuminoids", 2019 Fall National Meeting, Aug. 22-29, 2019, 1 pg.

* cited by examiner

*Primary Examiner* — Sikarl A Witherspoon

(74) *Attorney, Agent, or Firm* — Schwegman Lundberg & Woessner, P.A.

(57) ABSTRACT

The present invention provides compounds including curcuminoids and analogs thereof, as well as methods of making the same. In various aspects, the method of making the compounds is free of added solvents.

18 Claims, 19 Drawing Sheets

4 5 12

Functional Group Effect

Substitution Position Effect

21

20 22 23 21 keto enol 20
5
15

12g

12j

14a

Natural Symmetric Curumin

Unnatural Asymmetric Curuminoids: this Work

Side Arms Can be Modified Using Commercial Aldehydes

Non-equivalent Arms, ABC Type

Equivalent arms, ABA Type

Non-equivalent Arms, CBA Type $R^1=R^2=Cl$, AS4Cl
$R^1=R^2=Cl$, AS4OMe
$R^1=Cl, R^2=$ OMe, AS4Cl4OMe aldehyde ACHE asymmetric curcuminoid aldehyde ACPE asymmetric curcuminoid

CURCUMINOIDS, ANALOGS THEREOF, AND METHODS OF MAKING THE SAME

CROSS-REFERENCE TO RELATED APPLICATION

This application claims the benefit of priority to U.S. Provisional Patent Application Ser. No. 63/221,768 filed Jul. 14, 2021, the disclosure of which is incorporated herein in its entirety by reference.

BACKGROUND

Curcuminoids and analogues thereof have a wide array of biological activities. However, conventional synthetic approaches to these compounds are limited, suffer from poor yield and lack of efficiency, and are not environmentally friendly. Some curcuminoid and curcuminoid analogue structures cannot be achieved via conventional synthetic techniques.

SUMMARY OF THE INVENTION

The present invention provides a compound having the structure:

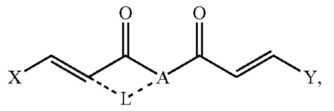

The variable A is —C—. The variables X and Y are independently chosen from substituted or unsubstituted aryl, and substituted or unsubstituted heteroaryl. The variable L is absent or is a substituted or unsubstituted linker group chosen from $—(CH_2)_3—$ and $—(CH_2)_2—$.

The present invention provides a method of making the compound having the structure:

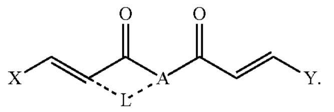

The method includes combining (a) acetylacetone, 2-acetylcylohexanone, 2-acetylcyclopentanone, or 2-acetylcyclohexane-1,3-dione; (b) an aldehyde having the structure X—C(O)H and/or Y—C(O)H; (c) $B_2O_3$; (d) $R^B—NH_2$; and (e) $(R^BO)_3B$; to form the compound. The variable $R^B$ is independently $(C_1\text{-}C_{10})$alkyl.

The present invention provides a method of treating a disease. The method includes administering an embodiment of the compound described herein to a subject that has the disease.

The present invention provides a method of killing a microbe or decreasing the rate of proliferation of a microbe. The method includes contacting the microbe (e.g., a bacteria or virus) and an embodiment of the compound described herein.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
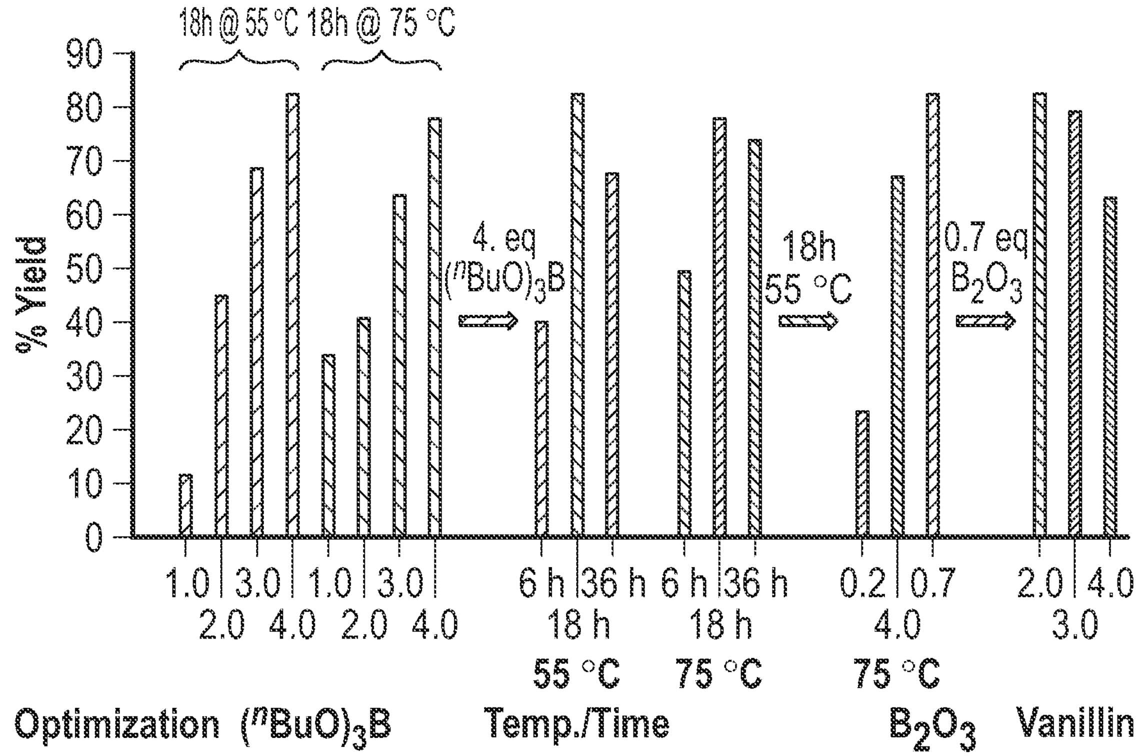
FIG. 1 illustrates an optimization of a solvent-free methodology, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, $OC(O)N(R)_2$, CN, $CF_3$, $OCF_3$, R, C(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, C(=NOR)R, and substituted or unsubstituted $(C_1-C_{100})$hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, $OC(O)N(R)_2$, CN, NO, $NO_2$, $ONO_2$, azido, $CF_3$, $OCF_3$, R, O (oxo), S (thiono), C(O), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, and C(=NOR)R, wherein R can be hydrogen or a carbon-based moiety; for example, R can be hydrogen, $(C_1\text{-}C_{100})$hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, $-CH=CH(CH_3)$, $-CH=C(CH_3)_2$, $-C(CH_3)=CH_2$, $-C(CH_3)=CH(CH_3)$, $-C(CH_2CH_3)=CH_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to $-C\equiv CH$, $-C\equiv C(CH_3)$, $-C\equiv C(CH_2CH_3)$, $-CH_2C\equiv CH$, $-CH_2C\equiv C(CH_3)$, and $-CH_2C\equiv C(CH_2CH_3)$ among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R—NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, —NHR, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups. The term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$ hydrocarbyl means the hydrocarbyl group can be methyl $(C_1)$, ethyl $(C_2)$, propyl $(C_3)$, or butyl $(C_4)$, and $(C_0-C_b)$ hydrocarbyl means in certain embodiments there is no hydrocarbyl group. A hydrocarbylene group is a diradical hydrocarbon, e.g., a hydrocarbon that is bonded at two locations.

Compound.

In various aspects, the present invention provides a compound having the structure:

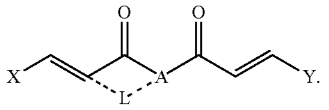

The variable A is —C—. The variables X and Y can each independently be chosen from substituted or unsubstituted aryl, and substituted or unsubstituted heteroaryl. The variable L can be absent or can be a substituted or unsubstituted linker group chosen from $—(CH_2)_3—$ and $—(CH_2)_2—$.

The compound can be a curcuminoid, and variable A can be —C—.

When the variable A is —C—, the carbonyl groups adjacent to A can together with A be in a keto form, an enol form, or a combination thereof. For enol forms, the hydroxyl can be formed from the right-hand carbonyl in the structures herein, or from the left-hand carbonyl in the structures herein.

The variable L can be absent. The variable L can be $—(CH_2)_3—$. The variable L can be $—(CH_2)_2—$. The variable L can be $—CH_2—CH_2—C(O)—$.

The variables X and Y can have the same chemical structure, or can have different chemical structures. The variables X and Y can be independently chosen from phenyl, 2-nitrophenyl, 3-nitrophenyl, 4-nitrophenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-hydroxyphenyl, 3-hydroxyphenyl, 4-hydroxyphenyl, 3,5-dimethoxyphenyl, 4-(trifluoromethyl)phenyl, 2-naphthyl, 6-methoxy-2-naphthyl, 3-methoxy-4-hydroxyphenyl, 2-hydroxy-3-methoxyphenyl, 4-cyanophenyl,

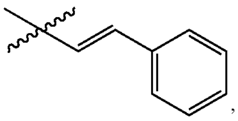
,
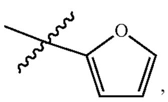
,
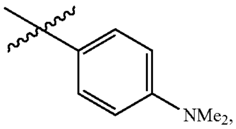

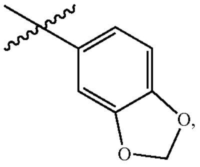
and
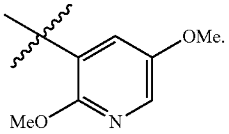

The variables X and Y can independently have the structure:

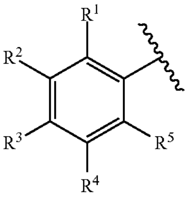

The variables $R^1$, $R^2$, $R^3$, $R^4$, and $R^5$ can be independently chosen from —H, $—OCH_3$, —Cl, —Br, —F, —I, —CN, $—NO_2$, $—CF_3$, and $—N(CH_3)_2$.

The compound can have the structure:

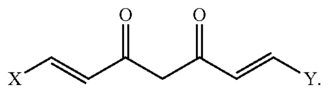

The compound can have the structure:

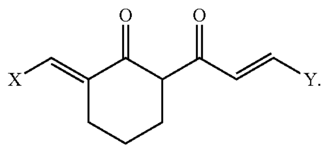

The compound can have the structure:

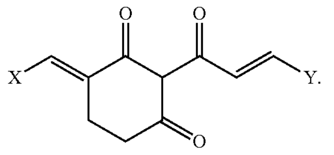

The compound can have the structure:

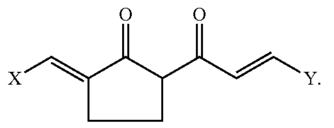

Method of Making Compound.

In various aspects, the present invention provides a method of making the compound described herein (e.g., curcuminoid or analog thereof), having the following structure:

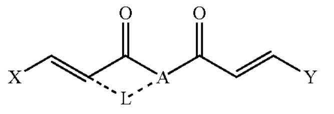

The method can include combining a) acetylacetone, 2-acetylcyclopentanone, and/or 2-acetylcyclohexane-1,3-dione, b) an aldehyde having the structure X—C(O)H and/or Y—C(O)H, c) $B_2O_3$, d) $R^B$—$NH_2$, and e) $(R^BO)_3B$. Combining the components is performed under conditions sufficient to form the compound having the structure above. The variable $R^B$ is independently ($C_1$-$C_{10}$)alkyl, such as n-butyl or isopropyl. The variable A is —C—. The variables X and Y can each independently be chosen from substituted or unsubstituted aryl, and substituted or unsubstituted heteroaryl. The variable L can be absent or can be a substituted or unsubstituted linker group chosen from $-(CH_2)_3-$, $-(CH_2)_2-$, and $-CH_2-CH_2-C(O)-$.

In some aspects, the method can be formed in the presence of an added solvent. In other aspects, the method and the combining of components a)-e) and any additional components is performed in the absence of any added solvent. The one or more aldehydes can be in a liquid state during the combining.

The method can include heating the combined components a)-e). The heating can be performed at any suitable temperature, such as to 10-150° C., or 40-100° C., or 70-90° C. The heating can be provided by any suitable source, such as a heater or a microwave (e.g., microwave energy). The combined components a)-e) can be heated for any suitable duration of time, such as 1 h to 5 d, or 10 h to 24 h.

Method of Treating a Disease.

Various aspects of the present invention provide a method of treating a disease. The method includes administering a compound of the present invention (e.g., curcuminoid or analog thereof) to a subject that has the disease. The administration of the compound treats the disease, such as by lessening the symptoms of the disease and/or by curing the subject of the disease. For example, the disease can be mononucleosis (caused by Epstein-Barr virus (EBV))

Method of Killing or Decreasing the Rate of Proliferation of a Microbe.

Various aspects of the present invention provide a method of killing a microbe and/or of decreasing the rate of proliferation of a microbe. The method can include contacting the microbe and a compound of the present invention (e.g., curcuminoid or analog thereof). For example, the microbe can be a bacteria.

EXAMPLES

Various embodiments of the present invention can be better understood by reference to the following Examples which are offered by way of illustration. The present invention is not limited to the Examples given herein.

Curcumin 1 is shown below.

Curcumin 1

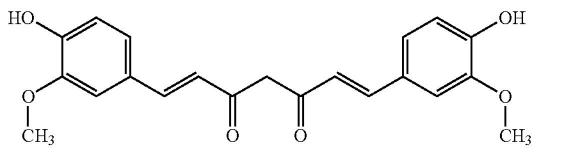

Part I. Symmetric Curcuminoid Synthesis.

Development of Curcumin Solvent-Free Synthesis.

To achieve solvent-free reaction conditions any solvent was eliminated, while the starting materials vanillin and acetylacetone were selected, and boron trioxide was used as the primary boron source.

An optimization of reaction parameters was conducted, and the results are summarized in FIG. 1, showing optimization of the solvent-free methodology using acetylacetone 4 (2.5 mmol), butylamine catalyst (10 mol %), varied amounts of vanillin, $B_2O_3$, and tri(n-butyl)borate under varied temperature and time. The nature of the amine was not modified as it was previously extensively investigated under solvent-based conditions.

Tri(n-butyl)borate was used for all experiments with the exception of tri(isopropyl)borate ester implemented in our mechanistic investigations.

Due to solvent-free conditions, monitoring of reaction mixtures could be performed using TLC or $^1$H NMR spectroscopy at any point in the synthesis. Reaction mixtures were quenched with water. Contrary to traditional approaches, no extensive extractions were required in this solvent-free method. The product was isolated using vacuum filtration resulting in curcumin 1 in high purity without need for further recrystallization or column chromatography.

Gradual variation of molar equivalents of $(n\text{-}BuO)_3B$ ranging from 1.0 to 4.0 (reaction temperature of 55° C. and time of 18 h were maintained throughout all trials), produced curcumin with yields varying from ~11 to 82% (Table 1, entries 1-6). In all reactions, a mixture of acetylacetone 4, $B_2O_3$ and $(n\text{-}BuO)_3B$ initially was heated in a vial at 55° C. for 20 min producing a nearly homogeneous suspension of intermediate 5. The increase of temperature to 75° C. generally resulted in a relatively small decrease in overall yield (Table 1, entries 7-12), providing curcumin in 34 to 78% yield. The optimal conditions observed at 75° C. employed 3 or 4 equivalents of borate ester. An exception to this trend was observed when 1.0 equivalent was used, however, this could be explained by decreased viscosity at 75° C. that facilitates reaction mixing. In general, the range of yields appeared to narrow at higher temperature, becoming less dependent on the equivalents of borate ester applied. Variation of time at each temperature provided lower product yields when either shorter or longer times were used (Table 1, entries 4-6 and 10-12). On average, shorter times were more detrimental to isolated yields than were longer reaction times (Table 1, entries 4 and 6, 10 and 12). Dry addition of vanillin and $n\text{-}BuNH_2$ catalyst was used in all reactions to ensure consistent volume of mixtures.

TABLE 1

Optimization of solvent-free synthesis of curcumin 1, by varying $(n\text{-}BuO)_3B$ quantities, reaction time and temperature, other reaction parameters were kept constant.

| Entry | $(n\text{-}BuO)_3B$, mmol | $(n\text{-}BuO)_3B$, equiv* | T (° C.) | Time (h) | % Yield, |
|---|---|---|---|---|---|
| 1 | 2.6 | 1.0 | 55 | 18 | 11.7 |
| 2 | 5.2 | 2.1 | 55 | 18 | 44.7 |
| 3 | 7.4 | 3.0 | 55 | 18 | 68.6 |
| 4 | 10.1 | 4.0 | 55 | 6 | 40.2 |
| 5 | 10.1 | 4.0 | 55 | 18 | 82.2 |
| 6 | 10.1 | 4.0 | 55 | 36 | 67.4 |
| 7 | 2.6 | 1.0 | 75 | 18 | 33.9 |
| 8 | 5.2 | 2.1 | 75 | 18 | 40.7 |
| 9 | 7.4 | 3.0 | 75 | 18 | 63.6 |
| 10 | 10.1 | 4.0 | 75 | 6 | 49.3 |
| 11 | 10.1 | 4.0 | 75 | 18 | 77.8 |
| 12 | 10.1 | 4.0 | 75 | 36 | 73.8 |

*Equivalents of tri(n-butyl)borate are calculated per quantities of acetylacetone used.

Using our optimized reaction conditions (Table 1, entry 5), the effect of varying quantities of boric anhydride and vanillin was studied. Reduction in the amount of $B_2O_3$ applied corresponded to a drastic drop in product yield (Table 2, entries 1 and 3). Product isolation was performed as described above. Unreacted aldehyde was isolated upon digestion.

TABLE 2

Optimization of solvent-free synthesis of curcumin 1 varying $B_2O_3$ quantities.

| Entry | $B_2O_3$, mmol | $B_2O_3$, equiv | Time, hrs | T, ° C. | Yield, % |
|---|---|---|---|---|---|
| 1 | 0.4 | 0.2 | 18 | 55 | 23.3 |
| 2 | 0.9 | 0.4 | 18 | 55 | 67.0 |
| 3 | 1.8 | 0.7 | 18 | 55 | 82.2 |

*Equivalents of boron oxide are calculated per quantities of acetylacetone used.

The increase of vanillin equivalents from a stochiometric ratio to 3 equivalents demonstrated no significant change in isolated yield of curcumin 1 when 3 equivalents were used (Table 3, entry 2). Product yield decreased somewhat moderately when 4 equivalents were applied (Table 3, entry 3).

TABLE 3

Optimization of solvent-free synthesis of curcumin 1 varying vanillin quantities.

| Entry | Vanillin, mmol | Vanillin, equiv | Time | T, ° C. | Yield, % |
|---|---|---|---|---|---|
| 1 | 5.0 | 2 | 18 | 55 | 82.2 |
| 2 | 7.5 | 3 | 18 | 55 | 79.3 |
| 3 | 10.0 | 4 | 18 | 55 | 63.3 |

*Equivalents of vanillin are calculated per quantities of acetylacetone used.

In summary, the developed solvent-free methodology has provided curcumin 1 with yields far exceeding the one reported by Pabon, H. J. A Synthesis of Curcumin and Related Compounds. *Rec. Trav. Chim.* 1964, 83, 379-386 with a substantial decrease in effort required for isolation and purification of the product as compared to conventional methods. In some cases, the obtained product yields were better than those observed for solvent-based methods.

Versatility of Solvent-Free Method to Obtain Symmetric Curcuminoids.

Figure 2:
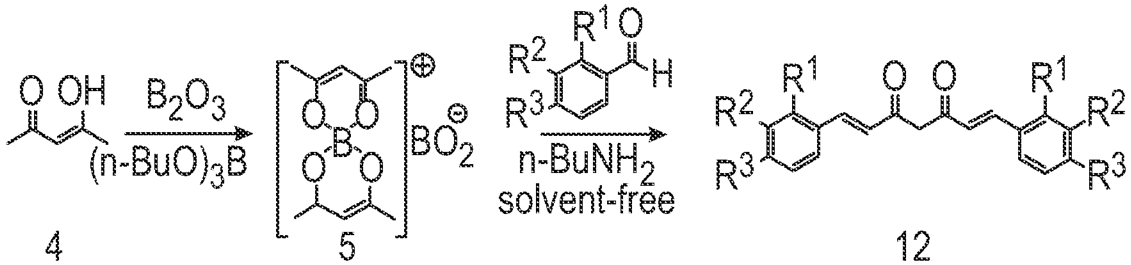
FIG. 2 illustrates a solvent-free protocol to obtain curcuminoids, in accordance with various embodiments.

Optimized conditions were applied to obtain a variety of curcuminoids 12a-j (FIG. 2, Table 4). Performance comparison was completed under mild and high heating conditions.

TABLE 4

Versatility of solvent-free protocol for the preparation of curcuminoids.

| | | | | | Isolated yields (%) | | | |
|---|---|---|---|---|---|---|---|---|
| | | Substituents | | | 55° C., | 55° C., | 75° C., | 75° C., |
| Entry | Code | $R^1$ | $R^2$ | $R^3$ | 18 h | 36 h | 18 h | 36 h |
| 1 | 12a | H | H | H | 21.17 | 14.10 | 14.31 | 11.00 |
| 2 | 12b | $NO_2$ | H | H | 30.62 | 27.23 | 34.50 | 44.50 |
| 3 | 12c | H | $NO_2$ | H | 38.20 | 41.80 | 39.50 | 48.70 |
| 4 | 12d | H | H | $NO_2$ | 28.42 | 17.22 | 30.10 | 39.71 |
| 5 | 12e | Cl | H | H | 40.80 | 30.84 | 46.26 | 39.36 |
| 6 | 12f | H | Cl | H | 57.54 | 70.65 | 80.99 | 70.65 |
| 7 | 12g | H | H | Cl | 67.49 | 80.02 | 69.68 | 60.85 |
| 8 | 12h | $OCH_3$ | H | H | 52.15 | 58.21 | 47.32 | 68.21 |
| 9 | 12i | H | $OCH_3$ | H | 51.20 | 54.30 | 41.27 | 56.11 |
| 10 | 12j | H | H | $OCH_3$ | 62.71 | 69.32 | 64.59 | 74.13 |

Substitution of vanillin with anisaldehydes did not require alteration of addition procedures despite the change in physical state between these two starting materials. Initial trials were conducted at 55° C. for 18 hrs using anisaldehydes with all other parameters identical to the previously described curcumin synthesis itself. An extension of the time from six hours to include overnight stirring demonstrated increased conversion on the TLC scale. The analysis of $^1H$ NMR of the crude mixture independently confirmed decrease of aldehyde, —C(O)H, signal at ~9 ppm while exhibiting the strong trans-coupling signals of the product along with other signals. Isolated yields were increased separately using both increased reaction time (55° C. and 36 hrs, Table 4 column 8) and increased temperature (75° C. and 18 hrs) (Table 4, column 7). The impact of those changes was not always positive (Table 4, entries 1 and 5). Use of unsubstituted benzaldehyde resulted in the decreased yield of 12a when time and temperature increases were applied.

However, an introduction of ortho-nitro group in the starting aldehyde for 12b the temperature increase had little to no effect, but the extended reaction time resulted in a nearly doubled overall yield. Trends for 12f and 12g were reversed, with formation of 12f being promoted by increased temperature while 12g was produced in higher yield after prolonged reaction time. Although, the reproducibility of each experiment was on acceptable level the overall pattern of yields seemed to be highly dependent on the functional group present in aldehyde as well as its location. To identify trends in performance of aldehydes data were grouped together to illustrate the effect of the functional group type (FIGS. 3A-C) and its location (FIG. 3D-F). Data are plotted using the colour code scheme to match the data listed in Table 4 and demonstrate versatility of the solvent-free protocol. Although in some cases (e.g., p-nitrobenzaldehyde, 17.22%, Table 4, entry 4 and FIG. 3A) an isolated product yield was lower than desired, this was easily overcome by a modification of a single reaction parameter.

Figure 3A:
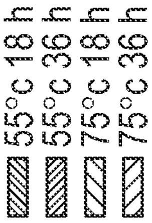
FIGS. 3A-3F illustrates a comparison of product yields under various conditions and using various substituents, in accordance with various embodiments.
Figure 3A:
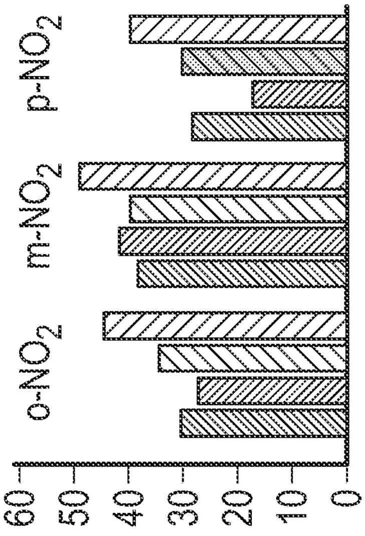
Figure 3B:
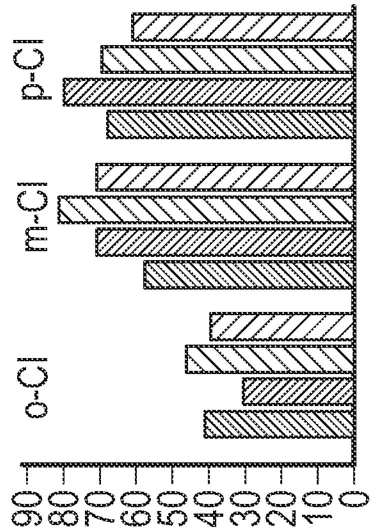
Figure 3C:
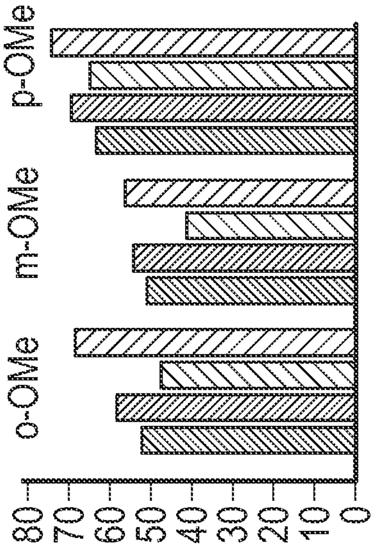
Figure 3D:
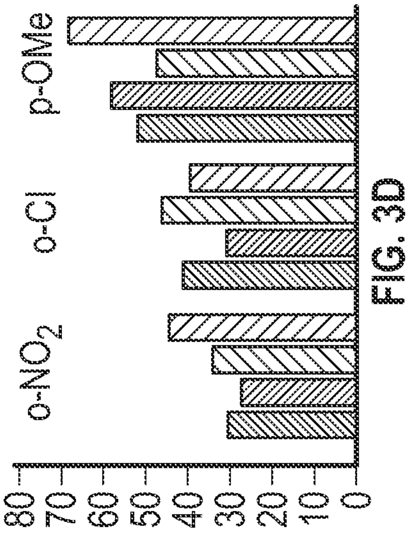
Figure 3E:
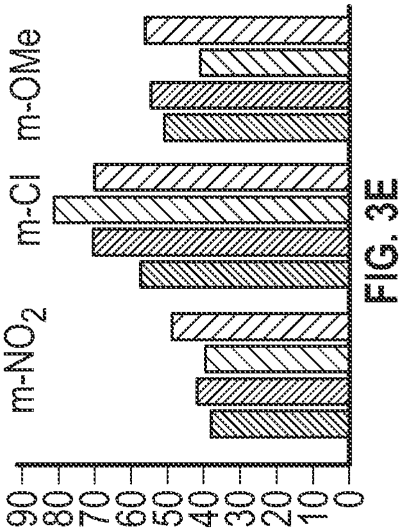
Figure 3F:
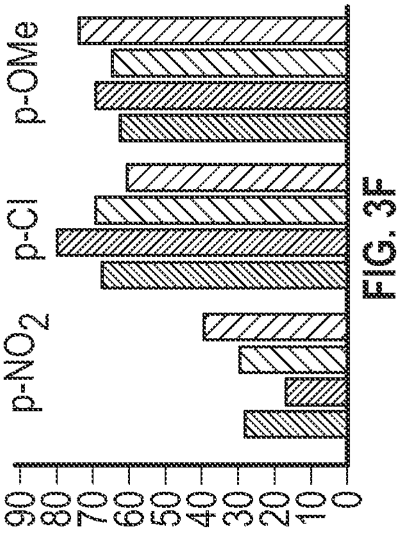

When using nitro- or methoxy-substituted benzaldehydes the best performance was observed for longer reactions at higher heat (Table 4, entries 2-4 and 8-10, FIGS. 3A and 3C). For chloro-substituted benzaldehydes the best product yields were obtained when using higher heat at a shorter reaction time with the exception of p-chlorobenzaldehyde (Table 4, entries 5-7, FIG. 3B). Use of temperatures higher than 75° C. were found to be unsuccessful resulting either in decomposition or in intractably thickened reaction mixtures. The increased viscosity complicated the work-up and required labour intensive separation of components without substantial impact on the desired product yields. The maximum duration of 36 hrs was chosen for practical reasons, although it could be considered as a parameter worth modifying if a particular reaction results in a lower yield in the future. In general, the direct comparison of the functional group for the solvent-free protocol was on par with that reported previously for the solvent-based reactions with anisaldehydes generally outperforming the nitro- and chloro-substituted aldehydes to produce yields of a wider spectrum. We were not able to identify a single trend connecting the variation of the substituent location and product yield (FIGS. 3D-F). Although para-substitution promoted the product formation when a methoxy- or a chloro-group was tested the corresponding nitro-compound was below those observed for the ortho- and meta-substituted analogues (FIG. 3F). Overall, the data demonstrate the efficiency of solvent-free methodology, in particular mild heat (55° C.) and longer time (36 hrs), towards the formation of a curcuminoid with a moderate to good yield regardless of the substitution type or its location.

Expansion of Solvent-Free Methodology.

Figure 4A:
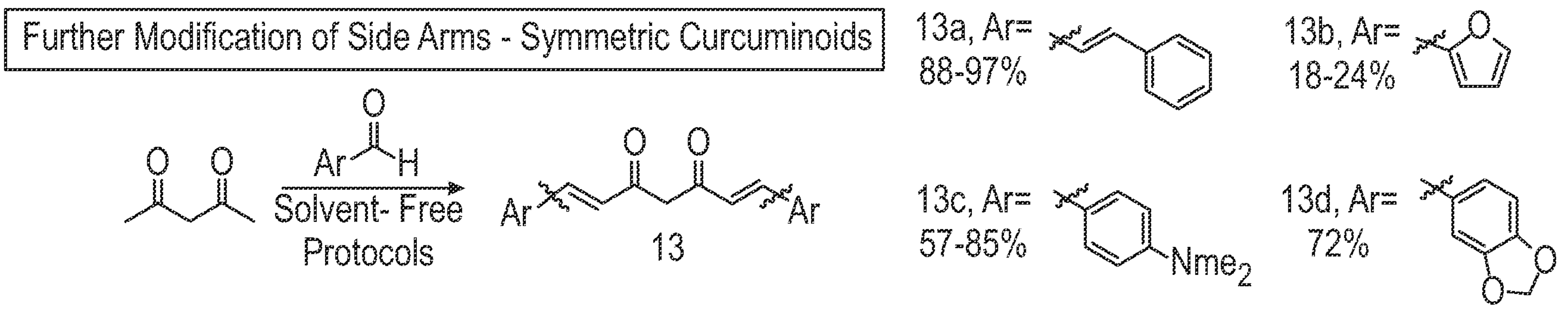
FIG. 4A illustrates a scheme showing further modification of side arms to give symmetric curcuminoids, in accordance with various embodiments.
Figure 4B:
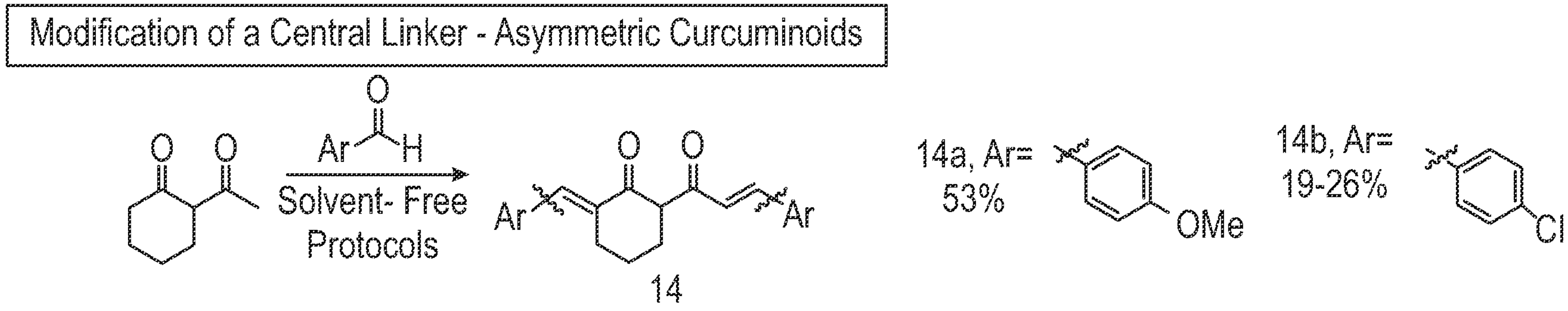
FIG. 4B illustrates a scheme showing modification of the central linker to give asymmetric curcuminoids, in accordance with various embodiments.

The scope was expanded to include substituted benzaldehydes with different functional groups (FIG. 4A) and a modification of a central linker (FIG. 4B). A longer reaction time of 36 hrs while testing both temperatures (55 and 75° C.) was utilized. Details are listed in Table 4. Cinnamaldehyde, furfural, p-dimethylaminobenzaldehyde, and piperonal were included. The protocol provided corresponding compounds 13a, 13c, and 13d in good to excellent yields (FIG. 4A, Table 4 entries 1, 3, and 4). Compound 13b was isolated in a low ~20% yield; however, it still exceeds the 8% reported by Pabon and did not require substantial alteration of a work-up procedure on our part.

An increase in the conjugated system, as in case of cinnamaldehyde, had a dramatic effect on the isolation of product 13a (FIG. 4A, Table 5, entry 1). Both reaction conditions provide an excellent yield, for comparison Pabon reported isolated yield of 29% for the same compound when conducting reaction at 50° C. in ethyl acetate for 4 hrs. Although in part our yield could be explained by the extension of the reaction time, the similar excellent performance of our method in case of piperonal indicates the benefits of solvent-free conditions (Table 5, entry 4). The isolated yield of product 13d was ~73% for both temperatures compared to 59% as previously reported by Pabon. The isolated yield for reactions of p-N,N-dimethylbenzaldehyde varied significantly with lower temperature resulting in a substantial decrease of the product yield (Table 5, entry 3). However, in both protocols product 13c was isolated with a better yield than previously reported (36%).

TABLE 5

Reaction outcomes for the expansion of solvent-free methodology.

| | | Time = 36 h Isolated % Yield | |
|---|---|---|---|
| Entry | Compound | 55° C. | 75° C. |
| 1 | 13a | 97.6 | 88.3 |
| 2 | 13b | 24.3 | 18.2 |
| 3 | 13c | 57.9 | 84.5 |
| 4 | 13d | 73.4 | 72.7 |
| 5 | 14a | 53.8 | 52.8 |
| 6 | 14b | 26.3 | 19.2 |

Translation of the solvent-free protocol to obtain asymmetric compounds was achieved by substituting acetylacetone with 2-acetylcyclohexanone (FIG. 4B). Two aldehydes were tested with other conditions used as described above for the curcumin synthesis itself. Data (Table 5, entries 5 and 6) demonstrate the general ease of translation of solvent-free protocol to obtain asymmetric curcuminoids 14a,b. p-Chlorobenzaldehyde did not perform as well as expected based on the data collected for acetylacetone reactions (Table 4, entry 7) where symmetric product 12g was isolated in ~70-80% yields across several solvent-free protocols while the analogous asymmetric 14b was produced in less than half the yield (~20-30%, Table 5, entry 6).

Hydroxy-Substituted Starting Materials.

The general success of our solvent-free approach did not translate to reactions involving hydroxy-substituted benzaldehydes as starting materials (Table 6, for synthesis see FIG. 2). In particular, all four protocols failed to provide appreciable amounts of isolated product for the ortho-hydroxybenzaldehyde starting material (Table 6, entry 1). “Traces” indicates that a majority of the starting material, either in the free or B-bound form, was isolated upon quenching of reaction mixtures using vacuum filtration by addition of water-ethyl acetate mixture. Alterations of isolation procedure allowed us to isolate the desired compound this is an apparent limitation of our method. Meta- and para-hydroxybenzaldehyde provided product without alteration of the work-up protocol but yields remained low (Table 6, entries 2 and 3).

TABLE 6

Hydroxy-substituted starting materials.

| | | | | | Isolated yields (%) | | | |
|---|---|---|---|---|---|---|---|---|
| | | Substituents | | | 55° C., | 75° C., | 55° C., | 75° C., |
| Entry | Code | $R^1$ | $R^2$ | $R^3$ | 18 h | 18 h | 36 h | 36 h |
| 1 | 12k | OH | H | H | traces | traces | traces | traces |
| 2 | 121 | H | OH | H | 26.11 | 25.17 | 32.41 | 23.64 |
| 3 | 12m | H | H | OH | 31.40 | 16.32 | 28.71 | 19.22 |

Mechanistic Study and Isolated Intermediate.

To the best of our knowledge there is no published step-by-step synthetic mechanism investigation for the formation of curcumin or related compounds using vanillin, boric anhydride, borate ester, and amine catalyst under solvent-based or solvent-free conditions.

Figure 5:
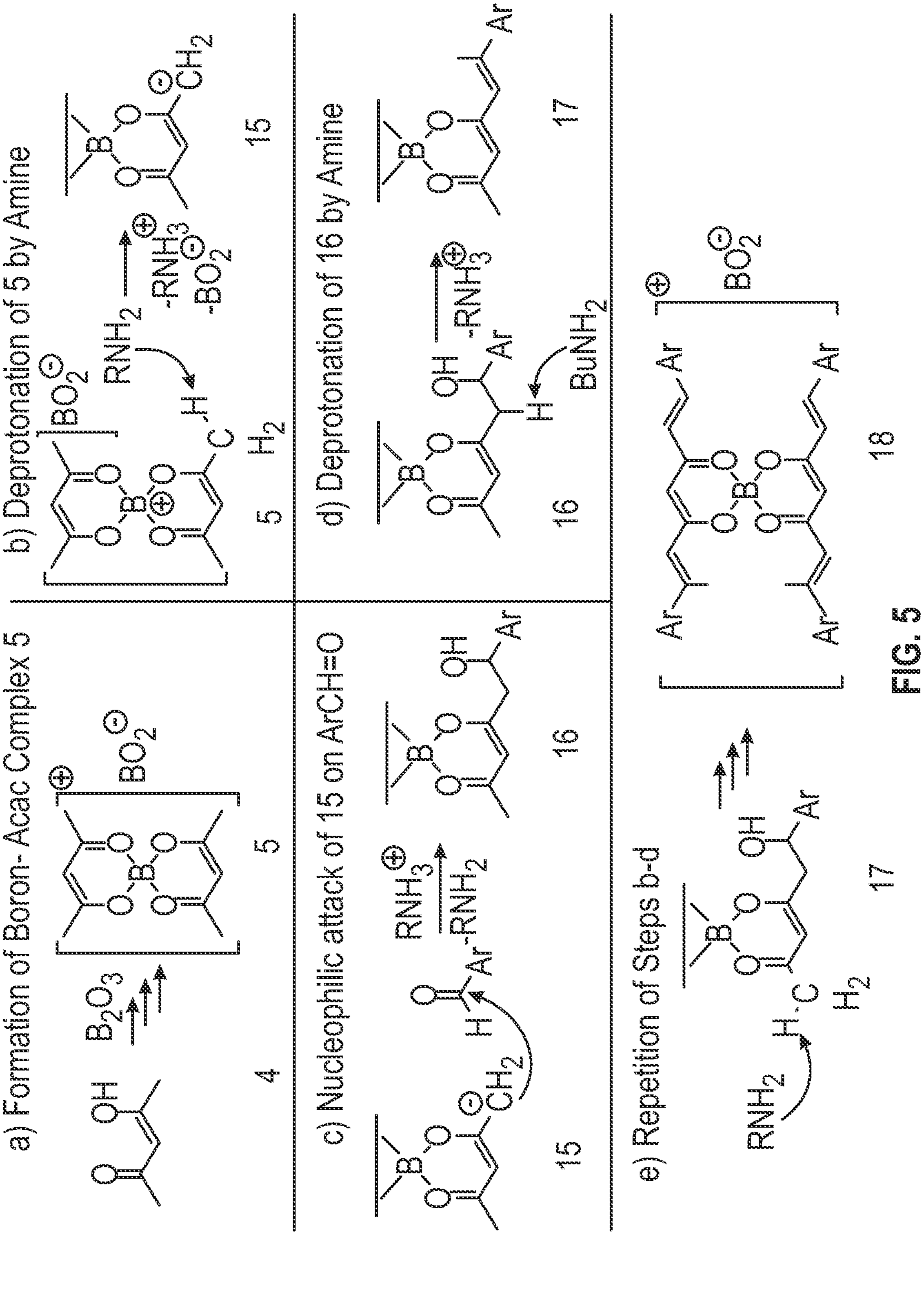
FIG. 5 illustrates a summary of mechanistic benchmarks based on proposed intermediates 5 and 18, in accordance with various embodiments.

Using a basic understanding of the condensation reactions and assuming a strict assignment of the amine solely as a base one can identify the main benchmarks of the potential mechanism (FIG. 5) as follows: a) formation of the boron-acetylacetone complex 5 b) deprotonation of intermediate 5 by amine producing enolate-type intermediate 15, c) nucleophilic attack on aldehyde resulting in the mono-condensation product 16, d) repeat of the deprotonation step providing intermediate 17, e) repeat of steps b-d resulting in rosocyanin type compound 18. Cleavage of 18 under acidic or basic conditions would release free curcuminoid, this step is not shown as it is not applicable to our solvent-free protocol. The outlined mechanism is dependent on the structures of intermediates 5 and 18, and to the best of our knowledge has not been discussed before. The formation of an intermediate 5 eliminates the potential for Knoevenagel condensation due to preceding deprotonation at the methylene carbon. Although the formation of complex 5 is widely accepted, it has not been isolated and there is no reported crystal structure of this compound. The role of this amine in the process is unclear. Amine is usually listed as a catalyst or a base source; however, experimental data of Krakov, M. H.; Edward, B. H. Process for the Synthesis of Curcumin-Related Compounds. U.S. Pat. No. 5,679,864, 1997 and Pabon independently demonstrated that only primary and secondary amines are efficient catalysts in the reaction. In addition, the emphasis on maintaining a low and consistent concentration of amine was noted but the recycling of the catalyst has not been previously discussed.

Figure 6:
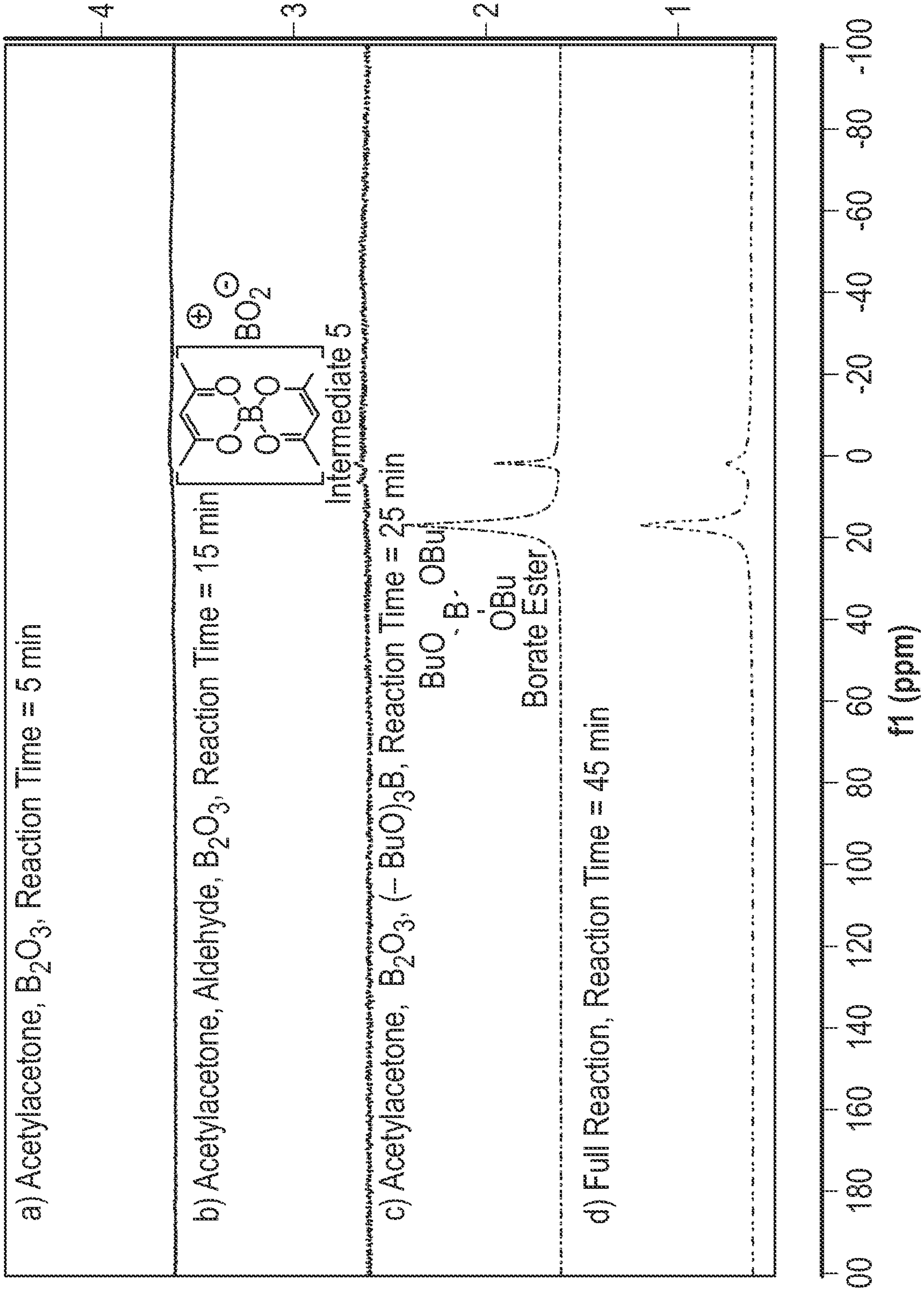
FIG. 6 illustrates a $^{11}B\{^1H\}$ NMR data supporting in situ formation of intermediate 5, in accordance with various embodiments.

Our efforts focused on identifying potential catalytic cycles in the curcuminoid synthesis. Initial attempts targeted the confirmation of the formation of complex 5. Reaction mixtures leading to products curcumin 1 and curcuminoids 12h-j were used as model experiments. A mixture of acetylacetone 4 and $B_2O_3$ in stochiometric amounts was combined at room temperature and stirred for 10 minutes. The reaction produced a homogeneous paste, after heat release ceased a sample was dissolved in $CDCl_3$ and analyzed by $^{11}B$ NMR (FIG. 6 plots (a) and (b)) b). Poor solubility of complex resulted in high signal to noise ratio, but the collected data demonstrate a change in the boron environment and presence of two inequivalent boron atoms. After the addition of $(n\text{-}BuO)_3B$ occurred the solubility of intermediate 5 had drastically increased allowing for the improvement of spectrum quality (FIG. 6 plot (c)). The sample was taken as an aliquot via syringe and transferred into an NMR tube followed by addition of $CDCl_3$ through a septum. The reaction sample was heated at 55° C. for approximately 20 min producing a somewhat homogeneous solution of intermediate 5 in borate ester. The signal of the complex 5 modified upon addition of borate ester, however, remained relatively unchanged as time progressed (FIG. 6 plot (d)). Attempts to isolate intermediate 5 resulted in isolation of boric acid, $H_3BO_3$, as a previously unreported polymorph.

Figure 7:
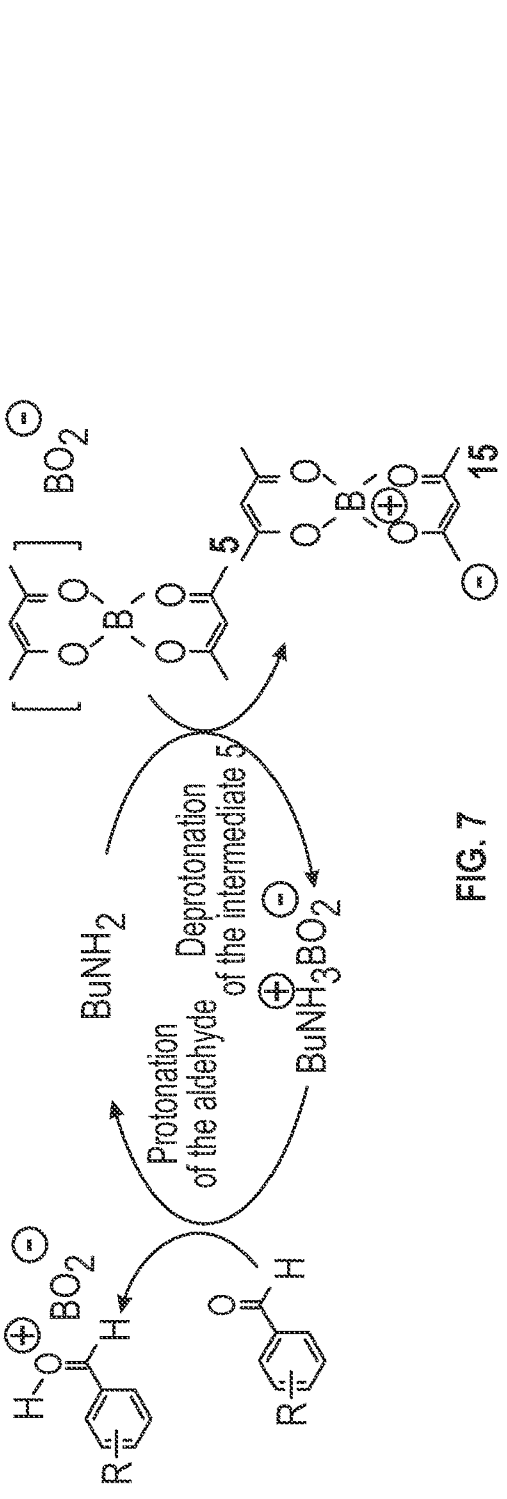
FIG. 7 illustrates use and regeneration of an amine catalyst in a general curcuminoid synthesis, in accordance with various embodiments.

A catalytic cycle involving an aldehyde, intermediate 5, and an amine (FIG. 7) was proposed. Our efforts employed a generic aldehyde and n-butylamine which could be easily translated to the use of another amine.

Figure 8:
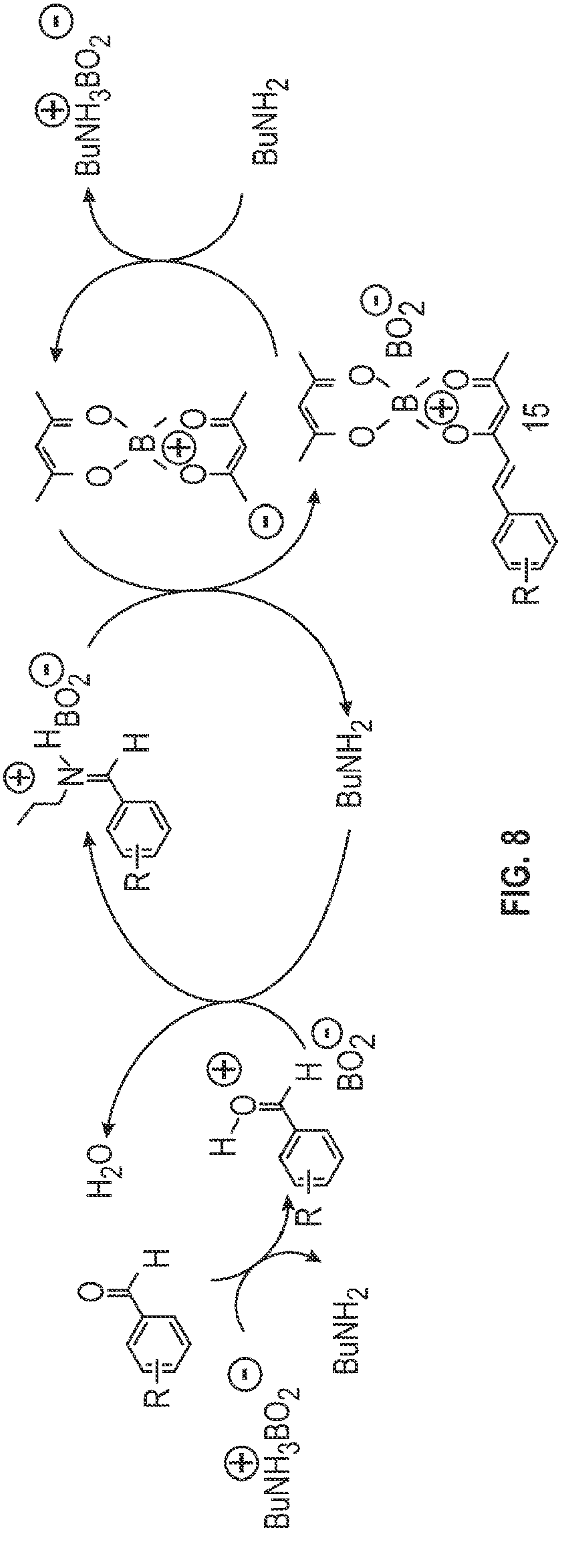
FIG. 8 illustrates a proposed alternative role of the amine as a catalyst in synthesis of curcuminoids, in accordance with various embodiments.

Literature data suggest that prior to the reaction of amine with intermediate 5, it undergoes Schiff base formation with the aryl aldehyde, ArCH═O. Several experimental observations support this idea. The possibility of converting imines to corresponding curcuminoids upon reaction with complex 5 was independently confirmed by others for solvent-based conditions and by us for solvent-free conditions. Since the imine (or iminium ion) formation can only occur with primary (or secondary) amines, it is not surprising that tertiary amines have been reported to be ineffective catalysts for curcuminoid formation. To the best of our knowledge, although the imine formation was speculated, there have been no investigations of in situ formation of imine/iminium-type intermediates in curcumin reaction mixtures. It appears also, there have been no attempts to propose an iminium-based catalytic cycle to explain the role of the amine and supporting compounds. Keeping in mind the protonation/deprotonation role of amine (outlined in FIG. 7) and adding the adjoining cycle to account for interaction of aldehyde and amine we suggest that the exchange of species follows the three-component catalytical cycle (FIG. 8). The new cycle fits in between the protonation of aldehyde (shown on the left) and the formation of the mono-addition product 15. The deprotonation of complex 5 is not included in the depicted cycle but is illustrated previously (FIG. 7).

Mechanistic studies were conducted using a full-scale reaction mixture setup. The reaction mixture consisting of acetylacetone 4, $B_2O_3$ and $(n\text{-}BuO)_3B$ was combined at room temperature and stirred for 10 minutes to achieve a nearly homogeneous solution. A sample was taken to confirm a change of the boron environment prior to proceeding to the next step. After formation of complex 5 was confirmed by NMR full amounts of vanillin or ortho-vanillin were added dry, followed by the first addition of $n\text{-}BuNH_2$ using syringe through a septum. The full amount of amine was divided in four portions to allow stepwise monitoring of changes, the alternative, extended dropwise addition of amine was avoided as an impractical route for NMR monitoring purposes. Immediately upon addition of amine a color change was observed, then reaction mixture was stirred for few minutes and an aliquot was taken via syringe and transferred into an NMR tube along with $CDCl_3$ added through a septum.

Figure 9:
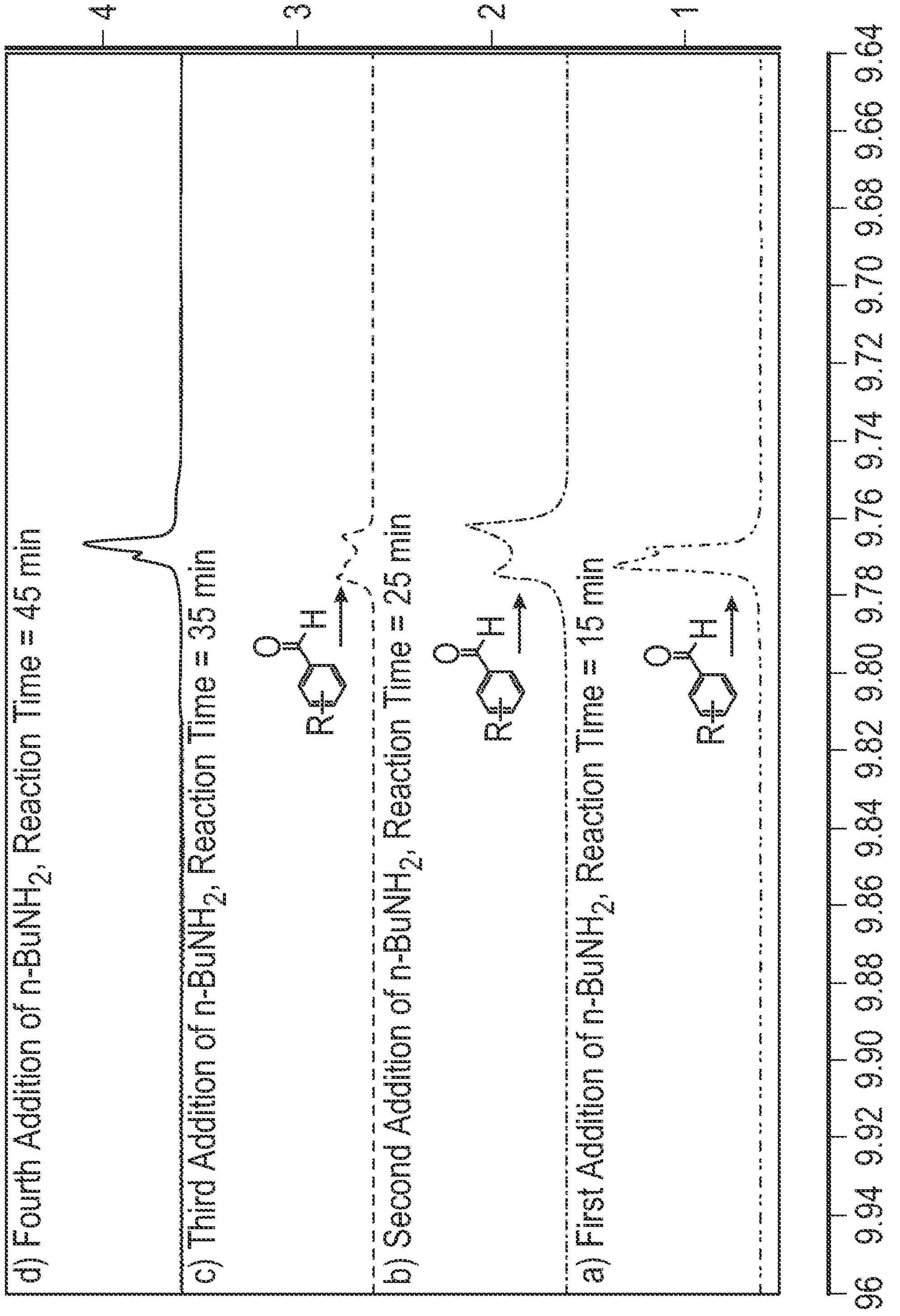
FIG. 9 illustrates $^1H$ NMR monitoring of in situ progress of curcumin 1 formation, in accordance with various embodiments.

The collected data clearly demonstrate that upon addition of the amine, the reaction occurs at the aldehyde and not at the sidearm of intermediate 5. The two signals appear to broaden with a second addition of amine, with an aldehyde signal still present but in lower quantity (FIG. 9 plot (b)). Upon third addition a further change occurs, and the third signal appears in the aldehyde range indicating potential formation of another intermediate (FIG. 9 plot (c)). As the reaction progresses after the last addition of amine the signal of aldehyde disappears and only two intermediate signals remain in the mixture (FIG. 9 plot (d)). Throughout the first 45 minutes of the reaction, no signals belonging to the bridging or enolic hydrogens [—C(=O)CH=C(OH)-] or trans-coupling signals were observed in the full spectra despite the blood red color of the reaction mixture. Further monitoring of the reaction at approximately one hour illustrated initiation of condensation between the unknown activated intermediates and complex 5 due to appearance of signals of trans-coupling bridge hydrogens.

Figure 10A:
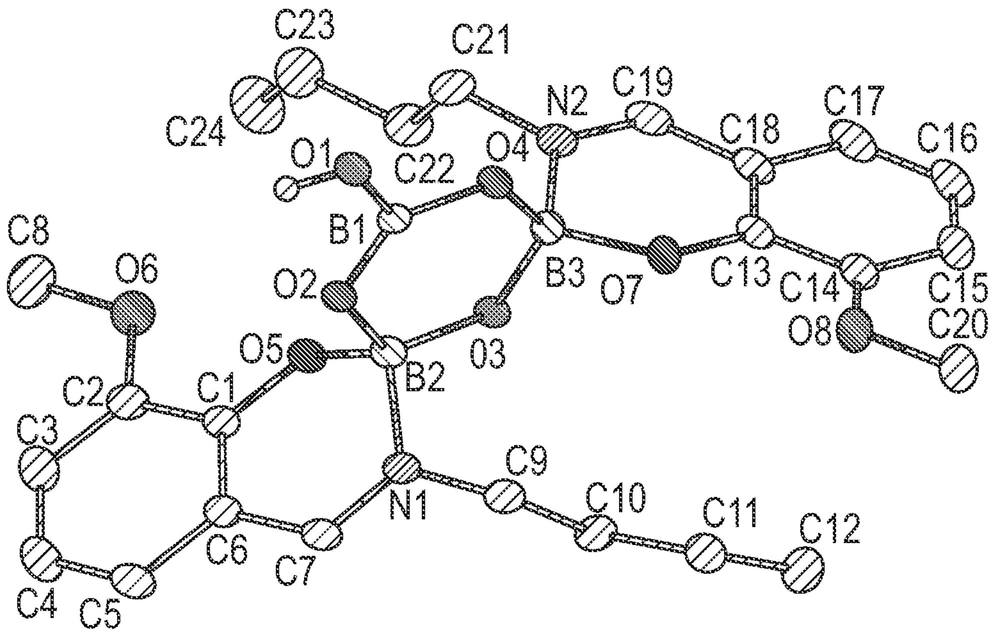
FIG. 10A illustrates a molecular drawing of 21·0.94 $CH_2Cl_2$ with the solvent molecule of dichloromethane omitted, in accordance with various embodiments. All non-H atoms are shown at 50% probabilities (all H atoms bound to C atoms are omitted)
Figure 10B:
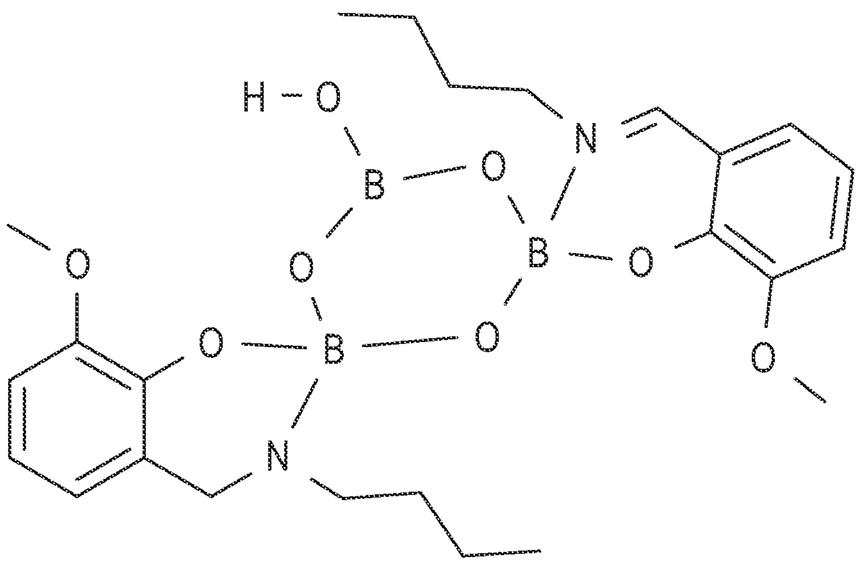
FIG. 10B illustrates a molecular drawing of compound 21, in accordance with various embodiments.
Figure 11:
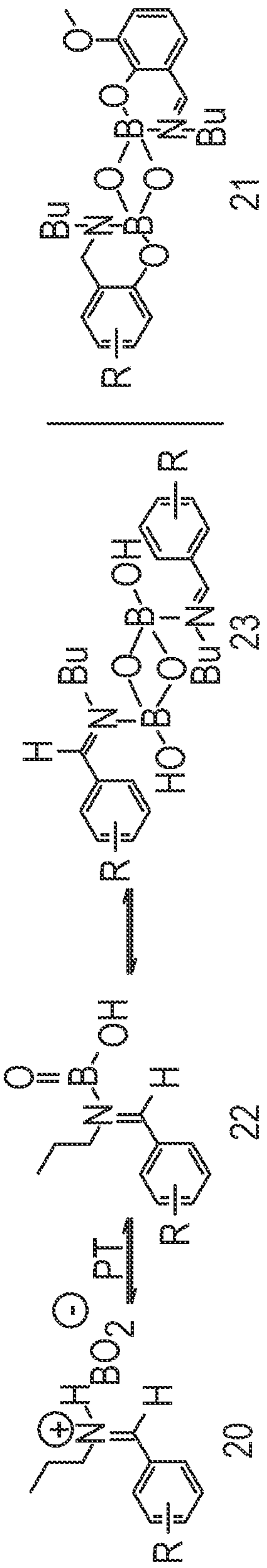
FIG. 11 illustrates a scheme showing a potential connection of amine catalytic cycle and the formation of an isolated imine-boron complex 21, in accordance with various embodiments.
Figure 12:
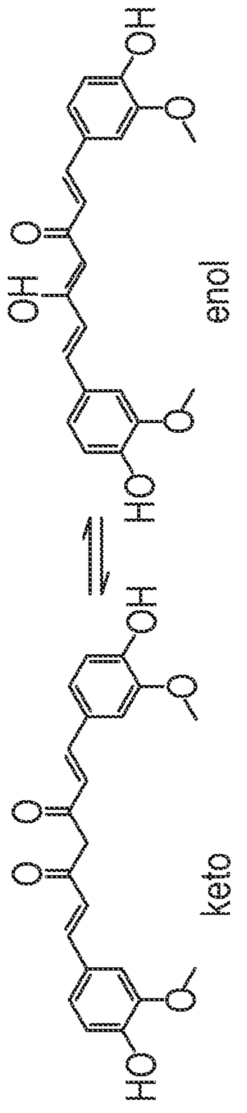
FIG. 12 illustrates keto-enol equilibrium of curcumin, in accordance with various embodiments.

Reactions were interrupted at different times by quenching with water and ethyl acetate mixtures. Obtained quenched reaction mixtures were separated using vacuum filtration. The solid products were subjected to crystallization using a variety of solvents. The best results were obtained using dichloromethane. The imine-boron complex 21 (FIGS. 10A-B) was isolated which provides support for the formation of an iminium intermediate for the first time and crystallographically characterize its co-crystal with $CH_2Cl_2$. The single-crystal structure of 21·0.94 $CH_2Cl_2$ unambiguously established the formation of a bond between the nitrogen and carbon atoms of the aldehyde. This indicates that nucleophilic attack on the aldehyde (FIG. 11) potentially is preceded by the formation of imine in the reaction mixture.

We suggest that the formation of compound 21 can be accomplished through a series of steps (FIG. 11) starting with aldiminium intermediate 20 that we previously introduced in FIG. 8. The aldiminium intermediate can undergo a proton transfer to form the neutral compound 22 in which nitrogen is bound to boron. Dimerization of complex 22 would provide the bridged product 24 where the nitrogen is still part of the imine component, but the boron portions are now shared between the two imine fragments.

Figure 13:
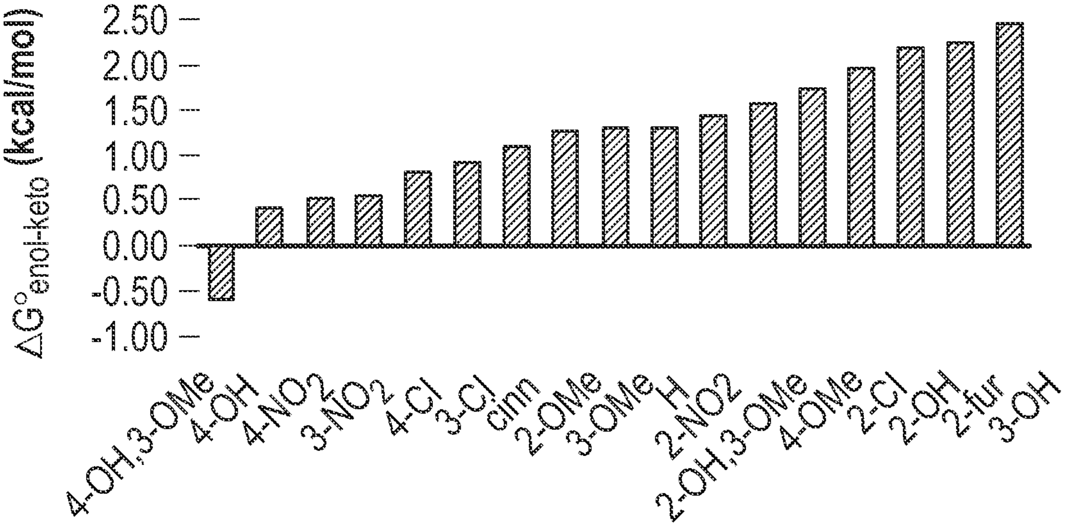
FIG. 13 illustrates tautomerization energies and free energy difference (labels) in kcal/mol, in accordance with various embodiments. Values provided by rank of least to greatest $\Delta G°$ (e.g., most enol-favored to most keto-favored).
Figure 14:
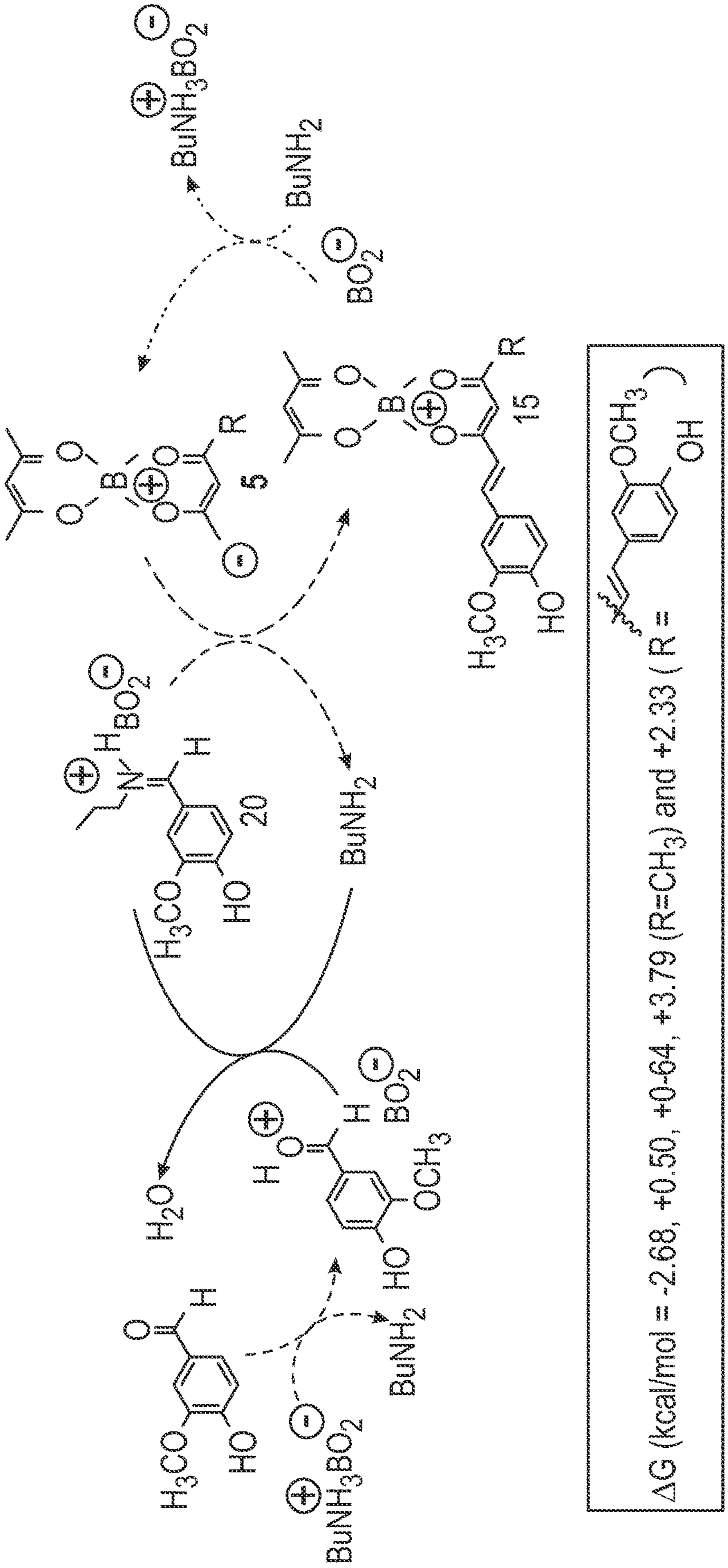
FIG. 14 illustrates net free energies (in kcal/mol) for each step of a proposed catalytic cycle, in accordance with various embodiments.

All structures from the proposed catalytic cycle (FIG. 8) were modeled. Compounds were modeled at the B3LYP/6-311++G level of theory and using the C-PCM method (FIG. 13). As shown in FIG. 14**, all steps are all energetically accessible, especially under the presumed heating conditions. Protonation of the aldehyde (−2.68 kcal/mol) is quite favorable as is the subsequent formation of the iminium ion (+0.50 kcal/mol). The requirement for the deprotonation of the ligated mono-addition (+2.33 kcal/mol) product is lower in energy versus acac itself (+3.79 kcal/mol).

Figure 15:
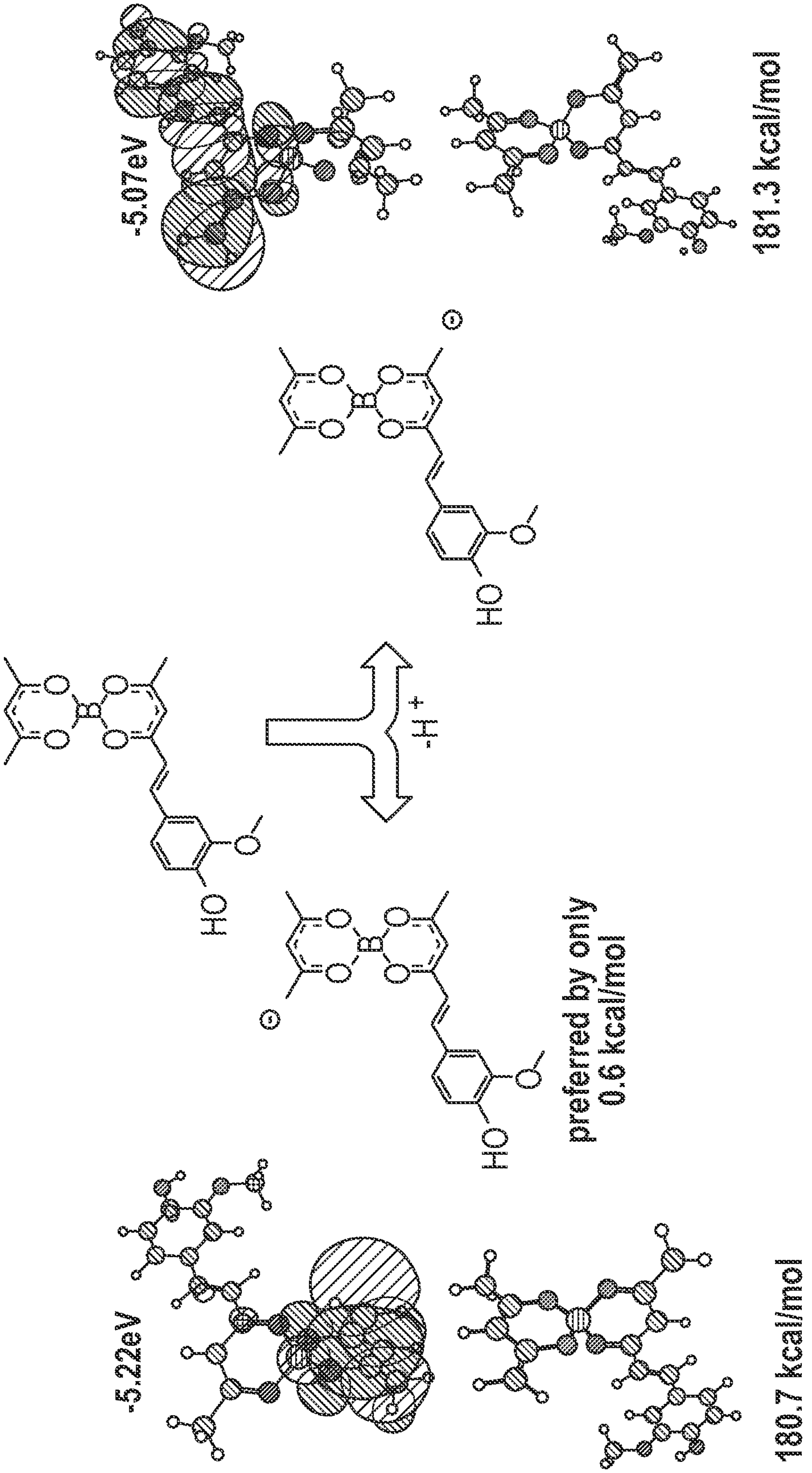
FIG. 15 illustrates optimized isomeric structures for deprotonated positions on the boron-coordinated monocondensation product, in accordance with various embodiments. HOMOs for both isomers clearly indicate the isolation of electron lone pair to one ligand only. Molecular orbitals depicted with contour value of 0.015.

The two possible deprotonation products (from the two distinct β-diketonate ligands) are nearly equivalent in energy, differing by only 0.62 kcal/mol (FIG. 15). This could imply a potential difficulty in obtaining mono-addition products.

Crystallographic Reports of Isolated Compounds.

Curcuminoids usually appear as colored powders and are often purified by recrystallization. Yet obtaining high-quality single crystals of these compounds suitable for structural analysis is often difficult.

Figure 16A:
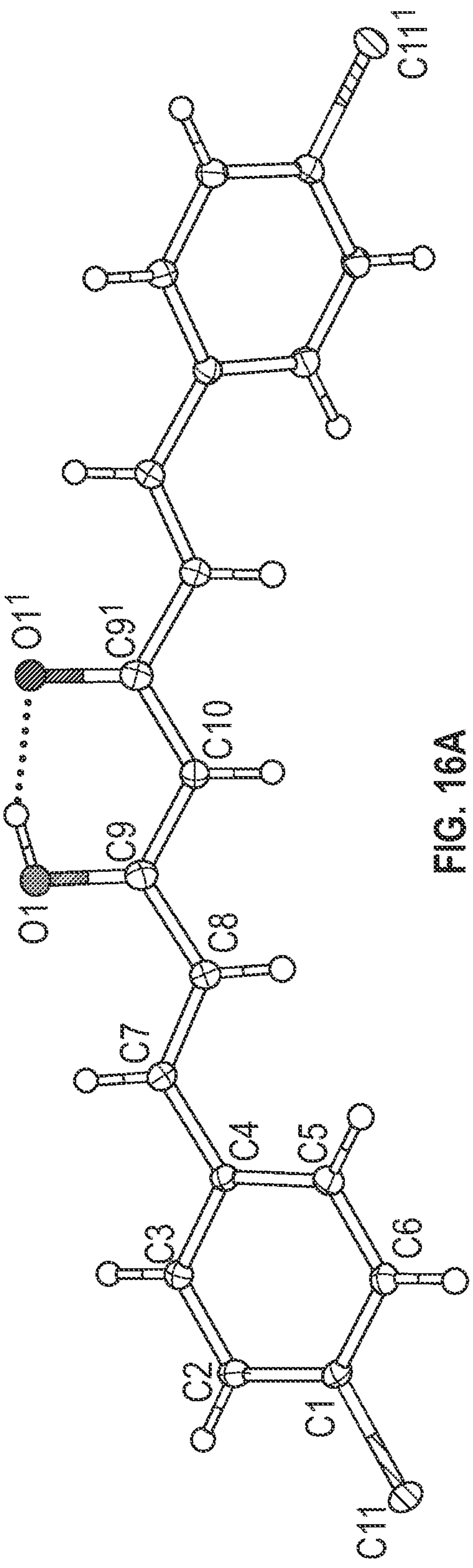
FIG. 16A illustrates a molecular drawing of compound 12g shown with 50% probability ellipsoids, in accordance with various embodiments. Symmetry code: i: −x, 1−y, z.
Figure 16B:
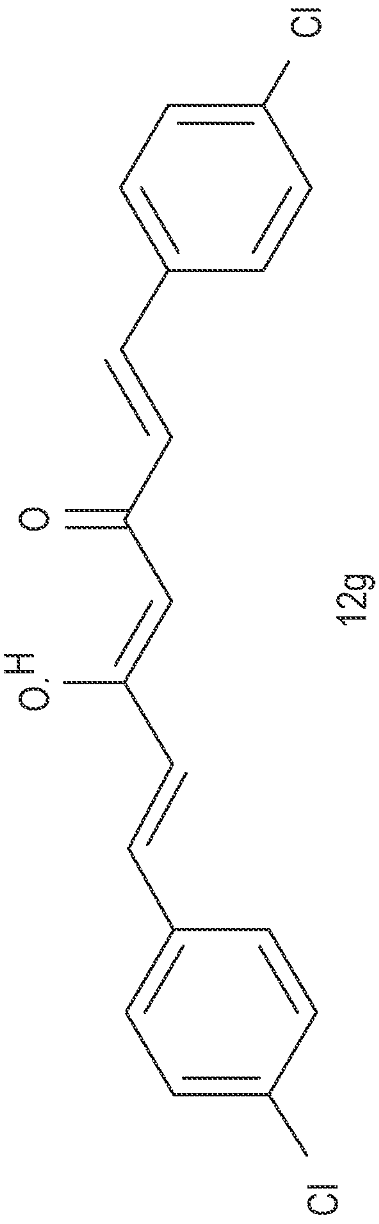
FIG. 16B illustrates the chemical structure of compound 12g, in accordance with various embodiments.

Single-crystal X-ray diffraction analysis of compound 12g (R=4-Cl) reveals that in the solid state the molecule exists as an enolic tautomer, FIG. 16A-B. The O—H . . . O interaction is characterized by a donor-acceptor distance of 2.514(2) Å and OHO angle of 158(4°). This correlates with the $^1$H NMR spectrum where a peak (d~17 ppm downfield to TMS) for the chelated hydroxyl group was observed.

Figure 17A:
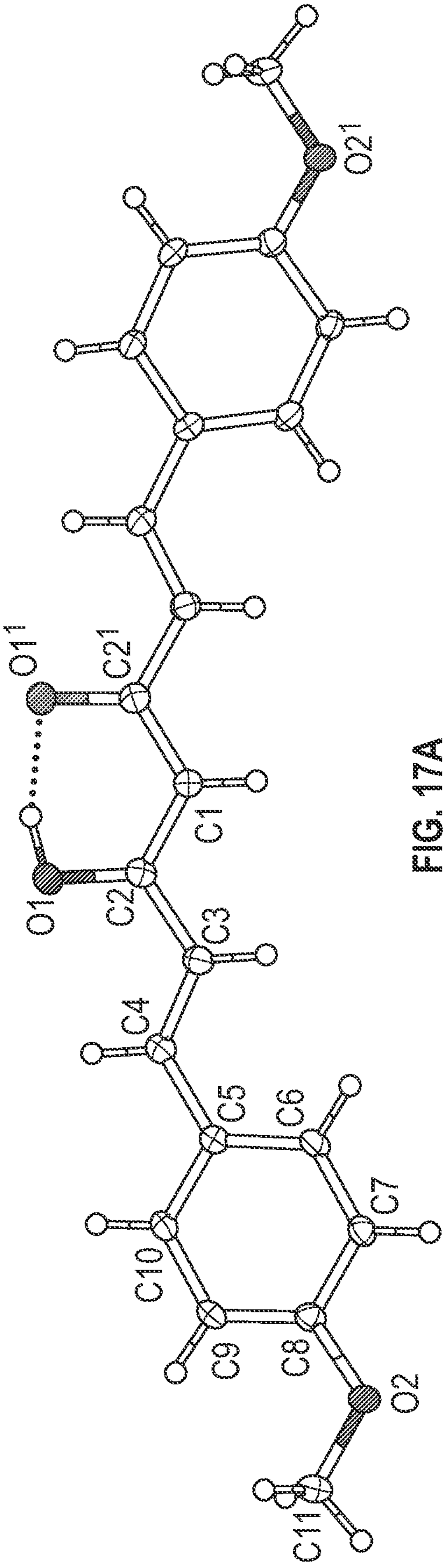
FIG. 17A illustrates a molecular drawing of compound 12j shown with 50% probability ellipsoids, in accordance with various embodiments. Symmetry code: (i) 1−x, y, 3/2−z.
Figure 17B:
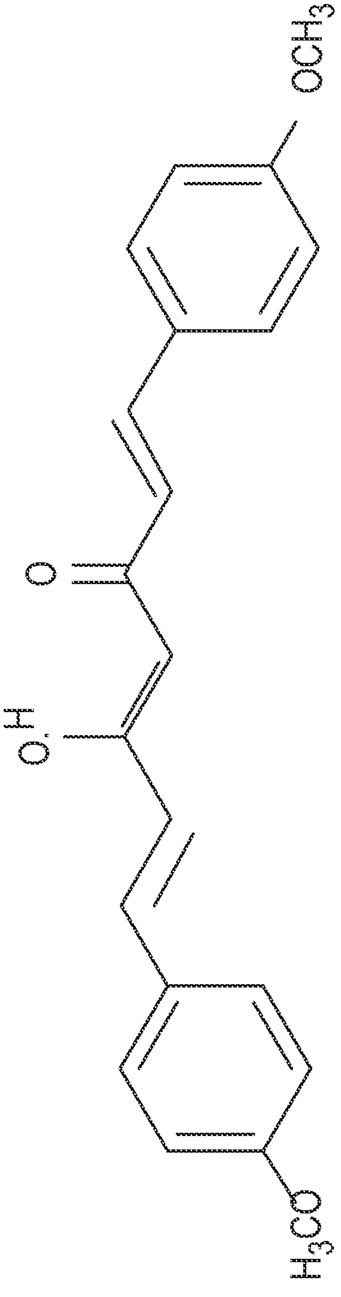
FIG. 17B illustrates the chemical structure of compound 12j, in accordance with various embodiments.

In the solid-state compound 12j (R=4-$OCH_3$) exists as an enolic tautomer with E-geometry of double bonds and the enolic double bond in Z geometry, FIGS. 17A-B. The 6-membered cyclic transition state between the two enolic forms involves an O—H . . . O hydrogen-bonding interaction with a donor-acceptor distance of 2.5048(15) and OHO angle of 159(3°). This correlates with the $^1$H NMR spectrum where a peak (d~16 ppm downfield to TMS) for the chelated hydroxyl group was observed.

Figure 18A:
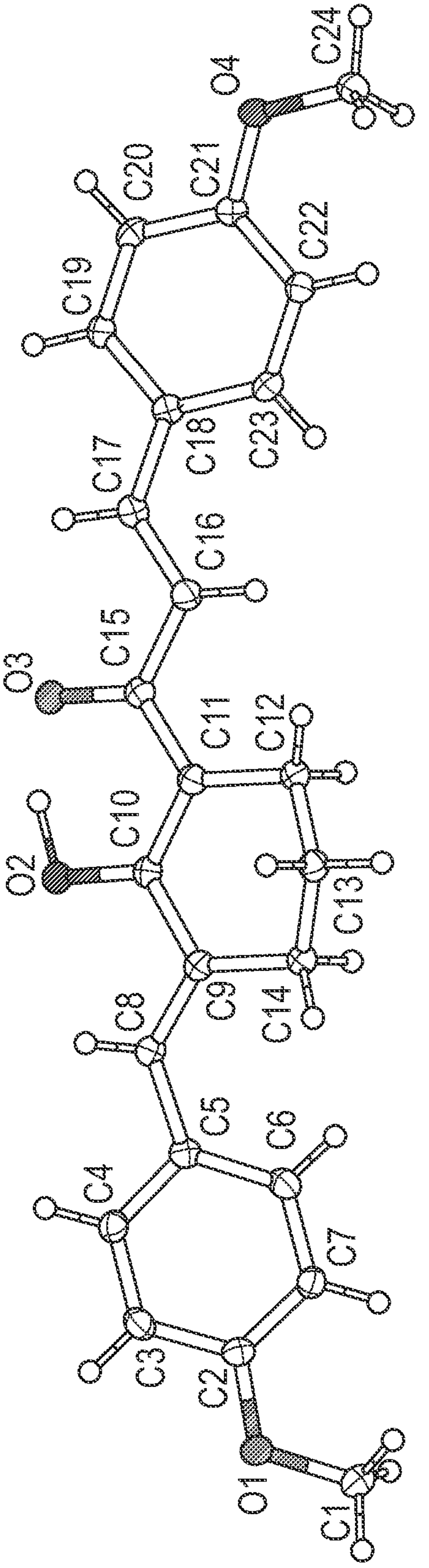
FIG. 18A illustrates a molecular drawing of compound 14a shown with 50% probability ellipsoids, in accordance with various embodiments.
Figure 18B:
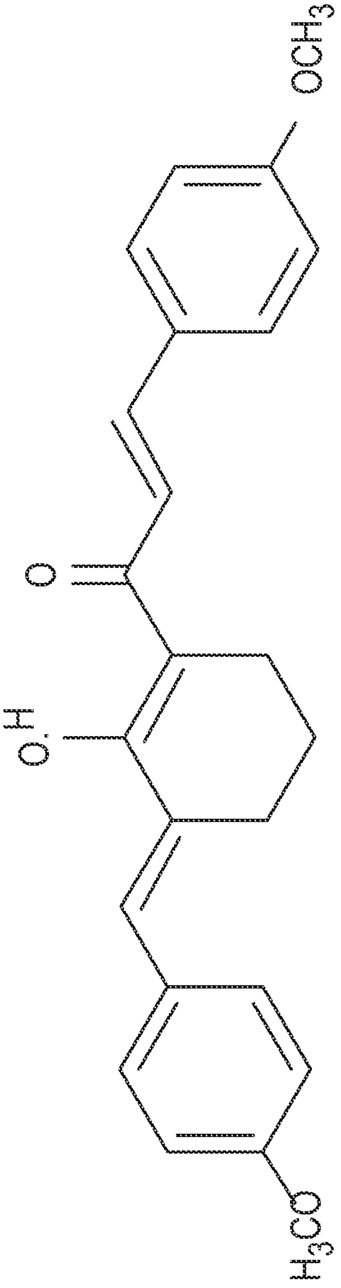
FIG. 18B illustrates the chemical structure of compound 14a, in accordance with various embodiments.

A single-crystal diffraction study of compound 14a (R=4-OMe) unambiguously established the geometries about the double bond, FIGS. 18A-B. In the solid-state the molecule exists as two enolic tautomers. The stereochemistries at the exocyclic and cinnamoyl double bonds were conclusively established as E; the enolic double bond showed the expected Z geometry due to the 6-membered cyclic transition state between the two enolic forms involving a hydrogen-bonding interaction between the carbonyl group and the enolic hydroxyl functionality. The O—H . . . O interaction is characterized by a donor-acceptor distance of 2.4433(10) Å and OHO angle of 158.0(19°). This correlates with the $^1$H NMR data where a peak (d~17 ppm downfield to TMS) for the chelated hydroxyl group was observed.

Part II. Development of One-Pot Solvent-Free Versatile Microwave Approach to Asymmetric Curcuminoids.

In the natural curcumin (FIG. 19) the skeleton is build using a central linker of acetylacetone and two equivalent arms formed from using vanillin as a starting commercial aldehyde (abbreviated as A). A solvent-free technology was adopted to include microwave-assisted organic synthesis. Despite substantial interest in curcuminoid synthesis there have been only two reports to date on application of microwave energy towards a hand-full of compounds. In both reports a domestic microwave was used limiting applicability and safety of protocols.

Figure 19:
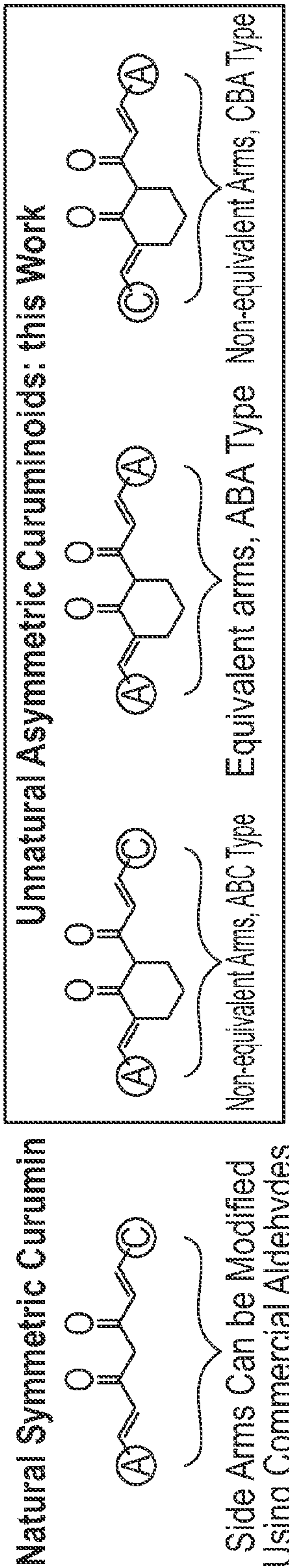
FIG. 19 illustrates natural symmetric curcumin as well as ABC, ABA, and CBA-type unnatural asymmetric curcuminoids, in accordance with various embodiments.

Solvent-free technology was adopted to be carried out using a single-mode microwave reactor. It was further extended it to obtain asymmetric curcuminoids (FIG. 19) by replacing acetylacetone linker with 2-acetylcyclopentanone (ACPE) or 2-acetylcyclohexanone (ACHE). While three possible compound types could be obtained in here, we report only on synthesis of asymmetric curcuminoids with equivalent arms (FIG. 19, ABA type).

In initial experiments ACHE and 4-methoxybenzaldehyde were used. The general trend of increased product formation with time was observed. The optimal average time was estimated at 11 minutes. Temperature variation was tested next. Temperatures of 45-65° C. resulted in lower product yields. Temperatures higher than 95° C. sped up reactions, however, upon digestions resulted in high viscosity mixtures. The best yields were consistently obtained for 85° C. Addition of catalyst at once decreased reaction performance. For microwave synthesis and 4-methoxybenzaldehyde no significant difference was observed when n-butylamine was added at once or in two to four portions. Modification of amounts of water scavenger were limited by the safety requirement of final reaction volume and were kept constant.

Figure 24:
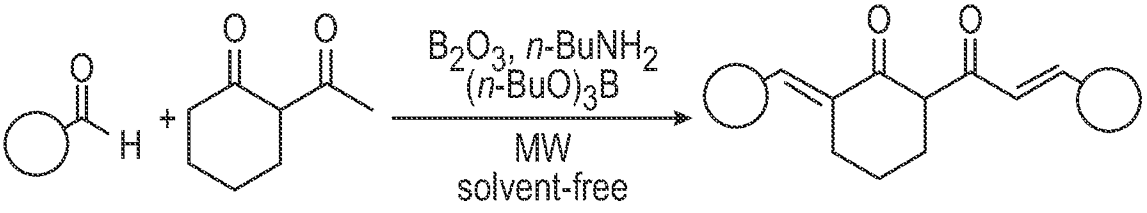
FIG. 24 illustrates a reaction of an aldehyde with ACHE to produce an asymmetric curcuminoid, in accordance with various embodiments.
Figure 25:
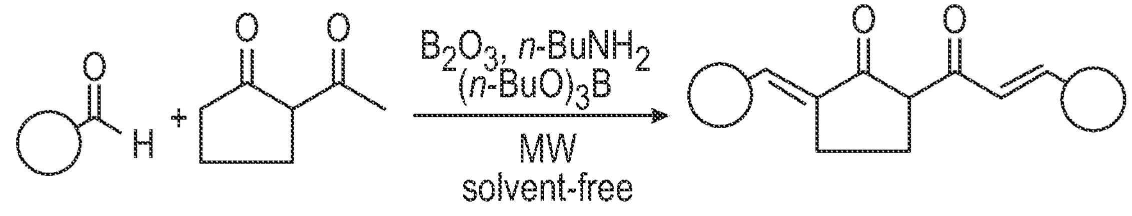
FIG. 25 illustrates a reaction of an aldehyde with ACPE to produce an asymmetric curcuminoid, in accordance with various embodiments.

The optimized procedure was further applied to include multiple commercially available aldehyde and 2-acetylcyclohexanone (ACHE, Table 7, FIG. 24) and 2-acetylcyclopentanone (ACPE, Table 8, FIG. 25). The listed yields are reported for optimized procedure to demonstrate versatility of the approach. However, for individual ligands yields could be improved using variations of temperature or time.

TABLE 7

Summary of utilized commercial aldehydes and 2-acetylcyclohexanone and isolated products yield (ABA type).

| Code | Aldehyde | Yield, % | m.p., ° C. |
|---|---|---|---|
| 1 | 2-methoxybenzaldehyde | 51 | 71.5-74.0 |
| 2 | 3-methoxybenzaldehyde | 43 | 108.3-109.7 |
| 3 | 4-methoxybenzaldehyde | 61 | 145.9-147.5 |
| 4 | 2-chlorobenzaldehyde | 55 | 99.1-101.2 |
| 5 | 3-chlorobenzaldehyde | 63 | 74-76 |

TABLE 7-continued

Summary of utilized commercial aldehydes and 2-acetylcyclohexanone and isolated products yield (ABA type).

| Code | Aldehyde | Yield, % | m.p., ° C. |
|---|---|---|---|
| 6 | 4-chlorobenzaldehyde | 35* | 177.1-179.7 |
| 7 | 2-nitrobenzaldehyde | 73 | 161.7-164.2 |
| 8 | 3-nitrobenzaldehyde | 35 | 166.4-172.5 |
| 9 | 4-nitrobenzaldehyde | 63 | 180.6-185.7 |
| 10 | 2-hydroxybenzaldehyde | traces | N/A |
| 11 | 3-hydroxybenzaldehyde | 67 | 151.2-155.5 |
| 12 | 4-hydroxybenzaldehyde | 81 | 260-263 |
| 13 | vanillin | 43 | redo |
| 14 | 2-vanillin | 5* | redo |
| 15 | benzaldehyde | 45 | 119.4-122.0 |
| 16 | 2-furfural | 52* | 148.8-151.4 |
| 17 | piperonal | 60* | 188.2-190.0 |
| 18 | 4-cyanobenzaldehyde | 90 | 228.5-231.0 |
| 19 | 4-(trifluoromethyl)benzaldehyde | 17 | 159.8-162.1 |
| 20 | 4-fluorobenzaldehyde | 47 | 133.2-135.3 |
| 21 | 4-(dimethylamino)benzaldehyde | 68 | redo |
| 22 | 3,5-dimethoxybenzaldehyde | 63 | 54-56 |
| 23 | trans-cinnamaldehyde | 43 | 164.6-167.1 |
| 24 | 6-methoxy-2-napthaldehyde | 77 | 219.7-221.8 |
| 25 | 2-napthaldehyde | 67 | 210.2-212.1 |
| 26 | 2,6-dimethoxypyridine-3-carboxaldehyde | 78 | 150.2-152.5 |

*Yields were improved by a modification of temperature or purification procedure.

TABLE 8

Summary of utilized commercial aldehydes and 2-acetylcyclopentanone and isolated products yield (ABA type).

| Code | Aldehyde | Yield, % | m.p., ° C. |
|---|---|---|---|
| 1 | 2-methoxybenzaldehyde | 77 | 176.6-178.7 |
| 2 | 3-methoxybenzaldehyde | 76 | 168.6-176.5 |
| 3 | 4-methoxybenzaldehyde | 61 | 203.2-205.5 |
| 4 | 2-chlorobenzaldehyde | 64* | redo |
| 5 | 3-chlorobenzaldehyde | 19 | 171.3-175.0 |
| 6 | 4-chlorobenzaldehyde | 45 | 219.4-227.6 |
| 7 | 2-hydroxybenzaldehyde | traces | N/A |
| 8 | 3-hydroxybenzaldehyde | 54* | redo |
| 9 | 4-hydroxybenzaldehyde | 69 | 252-253 |
| 10 | vanillin | 44 | 224.1-226.2 |
| 11 | benzaldehyde | 72 | 182.1-184.3 |
| 12 | 2-furfural | 60 | 134.3-136.4 |
| 13 | piperonal | 78 | 201.1-202.6 |
| 14 | 4-(trifluoromethyl)benzaldehyde | 21 | 200.8-203.7 |
| 15 | 4-fluorobenzaldehyde | 69 | 214.8-219.1 |
| 16 | trans-cinnamaldehyde | 79 | 220.6-223.2 |

*Yields were improved by a modification of temperature or purification procedure.

General Procedure

Boron oxide and a linker are mixed in a vial followed by addition of an aldehyde and borate ester. The ratio of reagents is varied based on the anticipated attachments. The reaction is carried out with conventional heating or in a microwave reactor after addition of catalytic amount of primary amine (e.g., butylamine). The microwave reactions take on average 7 to 8, and do not exceed 11 minutes. Reactions using conventional heating may require extended heating. Generally low temperatures favor formation of lower substitution. The isolation of products is conducted using a water digest, in some cases followed by bicarbonate wash. Filtration of product using Buchner filter provides nearly clean product. Air drying of products in an open beaker in the hood is shown to remove the majority of water. Samples for elemental analysis and yields calculations were usually dried in the vacuum oven at 68° C. overnight, temperatures exceeding 75° C. lead to decomposition. The substantial difference in solubility allows for fractional crystallization of higher substituted product in quantitative yields.

Part III. Other Studies on Symmetric and Asymmetric Curcuminoids.

Epstein-Barr virus (EBV) causes infectious mononucleosis, which is characterized by swollen lymph nodes, fever, sore throat, and severe fatigue. The virus remains at low levels for the lifetime of the infected person. Therefore, >90% of adults have been infected with EBV. EBV infection increases the risks of even more serious diseases. EBV infection can contribute to cancers, such as Burkitt lymphoma, Hodgkin lymphoma, and nasopharyngeal (back of the nose) and stomach carcinomas. People who have had EBV infectious mononucleosis have a higher risk for autoimmune disease multiple sclerosis (MS). Drugs against EBV have the potential to fight many human diseases. Previously tested curcuminoids do not have the chemical properties required of a drug to be given to humans.

Figure 20A:
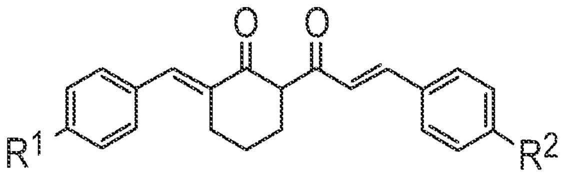
FIG. 20A illustrate various curcuminoids, in accordance with various embodiments.
Figure 20B:
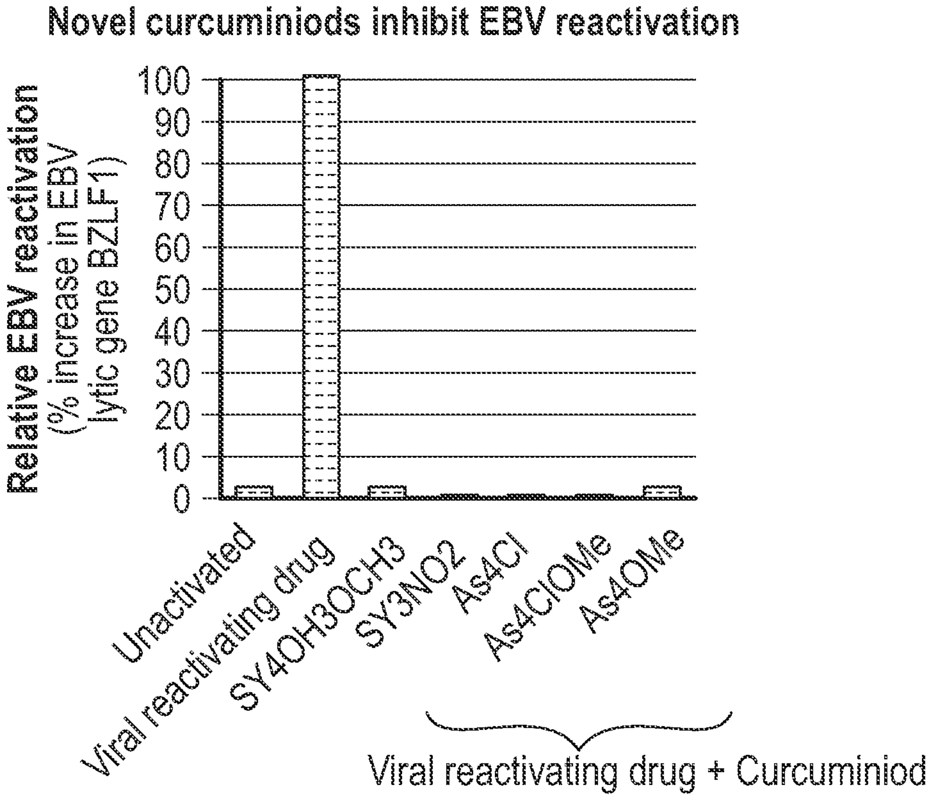
FIG. 20B illustrates EBV reactivation in the presence of the curcuminoids shown in FIG. 28A, measured by increased viral BZLF1 gene expression, is induced with a known reactivating drug, sodium butyrate (3 mM) compared to low expression in unactivated cells, in accordance with various embodiments. EBV reactivation was inhibited by five novel curcuminoids (10 μM).

Biological assays of the initial set of compounds demonstrated improved performance towards inhibition of Epstein Barr virus for most curcuminoids obtained (FIGS. 20A-B).

In a study applying our curcuminoids in combination with ultraviolet-A (UVA) light) towards inactivation of bacteria, such as *Escherichia coli, Staphylococcus aureus*, and Tulane virus (a human norovirus surrogate), our preliminary data demonstrate promising results of higher effects observed for demethoxycurcumin (DMC) and other asymmetric curcuminoids than those obtained for curcumin itself.

Part IV. Performance Comparison of Single-Mode and Batch Microwave Reactors Using Curcuminoid Synthesis.

Microwave experiments were performed using two most common microwave setups: a single-mode Biotage® Initiator+ synthesizer and a multi-mode MARS 5 digestion system. The Biotage® Initiator+ is equipped with a Robot Eight attachment. Each sample was run individually using standard 3-5 mL single-use microwave vials and volumes were maintained between 2.5 to 3.5 mL. All microwave vials were capped prior to placing in the instrument's cavity. Reaction parameters were monitored using instrument interface program. All syntheses involving MARS 5 digestion system were performed using 20 mL standard CEM vessels in a 16-vessel carousel. The total volume across all samples were maintained at 20-30 mL. Individual reactions volumes kept at 5.0 to 7.0 mL. All vessels were capped, however, due to the MARS vials' limitations the seal of the vials was not achieved. Several reactions were run side-by-side in the MARS reactor, the temperature probe was placed in the one to maintain temperature during the synthesis. No comparison between actual temperatures of other samples in the instrument cavity was made.

Typical Synthesis Using Single-Mode Biotage® Initiator+.

The reactions were carried out using the solvent-free procedure described in Part I, using conventional heating. The modifications were made to the isolation procedure to improve yields. Boric anhydride (0.1250 g, 1.80 mmol) and acetylacetone (0.257 mL, 2.50 mmol) were added into the microwave vial and stirred for 5 minutes at 350 rpm. After stirring an aldehyde (5.10 mmol), tri(n-butyl) borate (2.700, 10.0 mmol) and n-butylamine (0.100 mL, 1.00 mmol) were added to the microwave vial prior to sealing the vial. The vial was then placed on a stir plate and stirred for 15 seconds at 1200 rpm. The microwave vial was placed into the Robot 8 and the reaction was run for 85° C., 11:15 minutes, under high absorption, and 900 rpm stir rate, with activated cooling and FHT. Following the initial reaction and confirmation of product formation an ethanol digestion was run with the following conditions: 85° C., 22:32 minutes, high absorption, 900 rpm stir rate, cooling, and FHT. Product confirmation was completed using $^1H$ NMR ($CDCl_3$), TLC (hexane-acetone 2:1 eluent), and melting point. All data aligned with those previously reported.

Typical Synthesis Using Multi-Mode MARS 5 Digestion System.

The reactions were carried using the two-fold increase of the quantities used for the single-mode microwave experiments. The order of addition of all reagents and the external parameters, e.g., temperature and time, were kept identical between two instruments. No comparison between the pressure values or actual samples' temperatures between two instruments were possible. The modifications to isolation procedure were kept to a minimum to ensure validity of the yield. Rotation of vials used for the monitoring of temperature was made occasionally for different trials, however, no systematic modification of a temperature probe vessel was attempted. Following the initial reaction and confirmation of product formation an ethyl acetate digestion was run with the following conditions: 85° C. and 20 minutes. Product confirmation was completed using $^1H$ NMR ($CDCl_3$), TLC (hexane-acetone 2:1 eluent), and melting point. All signals in $^1H$ NMR spectra, melting point and $R_f$ values for isolated compounds aligned with those previously reported.

Environmental Impact Assessment

Figure 21:
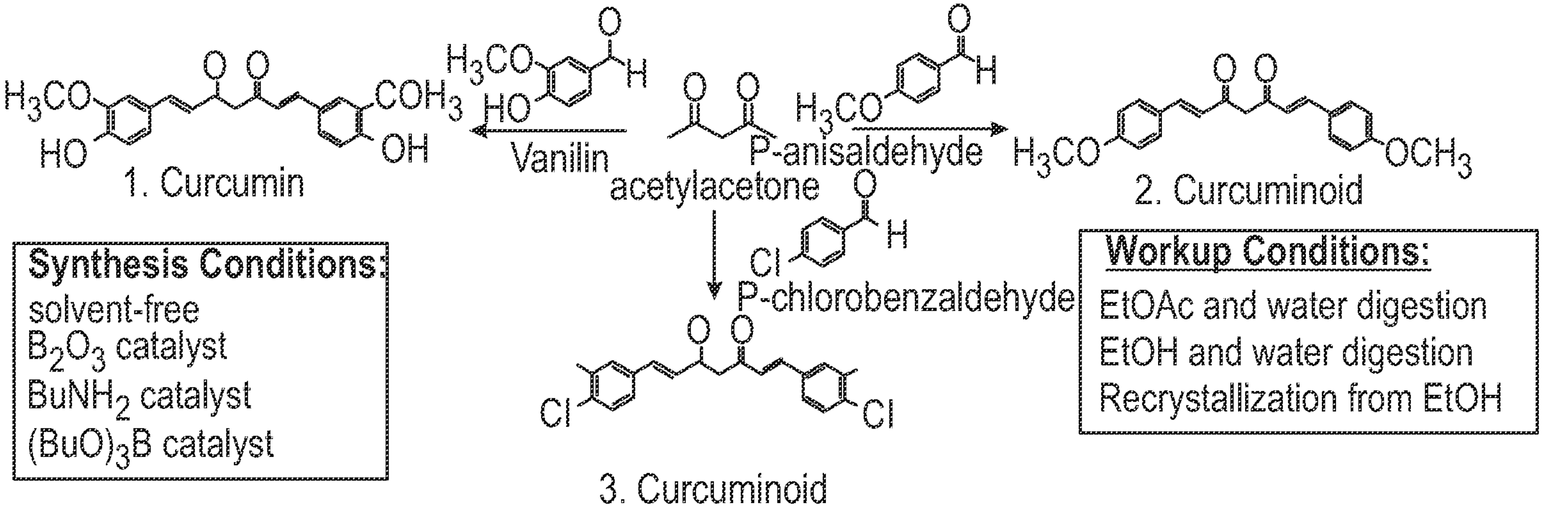
FIG. 21 illustrates various reactions showing the synthesis of curcumin and its close analogs, in accordance with various embodiments.
Figure 22:
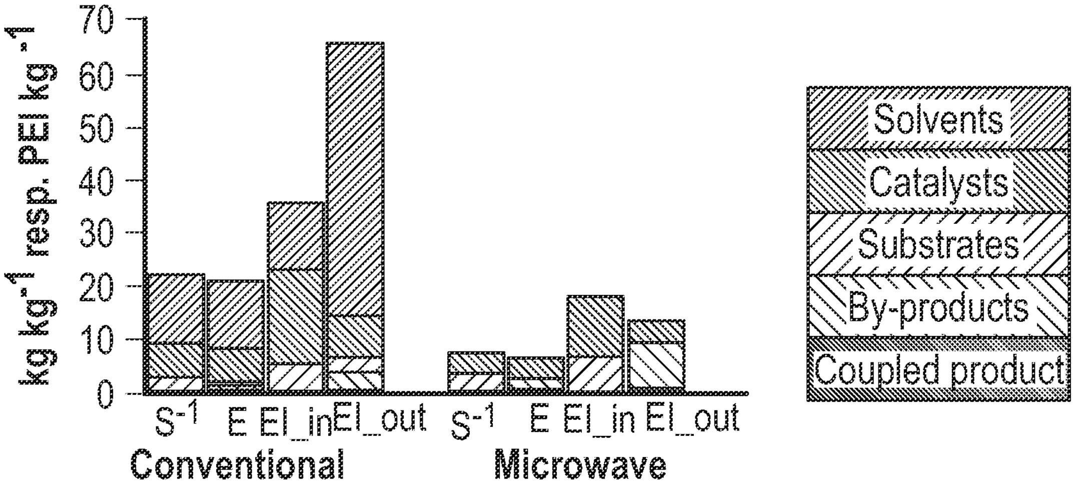
FIG. 22 illustrates environmental contributions of conventional heating solvent-based (on the left) and microwave-assisted solvent-free (on the right) methodologies excluding isolation steps, in accordance with various embodiments.
Figure 23:
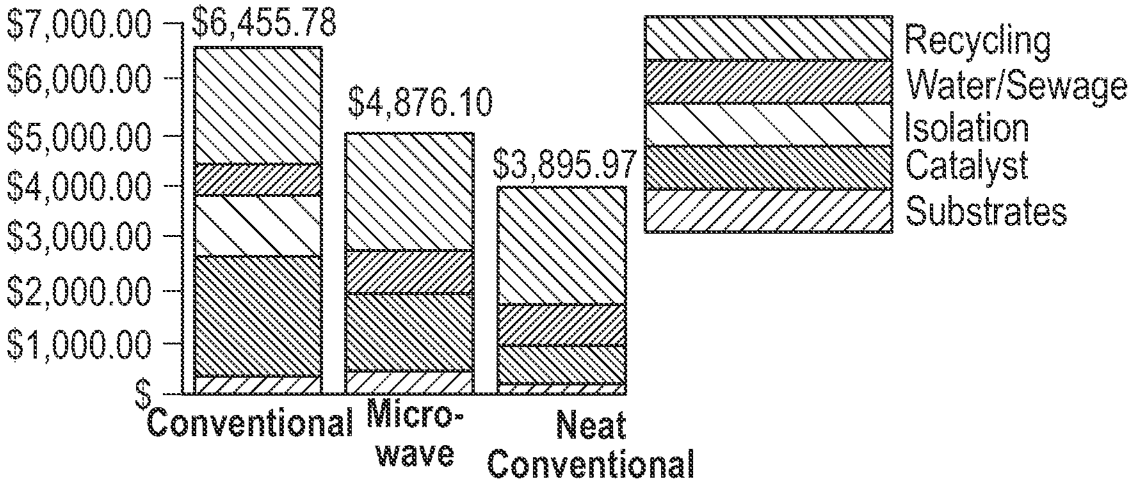
FIG. 23 illustrates a cost analysis of curcumin using three different methodologies, in accordance with various embodiments.

For environmental study all reagents listed in FIG. 21 for synthesis of curcumin 1 were utilized. Solvent-based synthesis with conventional heating in comparison to solvent-free microwave-assisted synthesis Environmental Assessment Tool for Organic Syntheses (EATOS) results in an approximate two-fold decrease in material necessary to make 1 kg product $s^{-1}$, waste per kg product E, and environmental index of input materials when using the microwave solvent-free synthesis (FIG. 22). The largest change was with the environmental index of the output material which the microwave solvent-free method decreased by an approximate factor of 3.5 (FIG. 22). EATOS was also used to calculate the cost to produce 1 kg of product from each method. The cost production of the solvent-based protocol with conventional heating decreased from $6,455.78 to $4,876.10 when using the microwave-assisted solvent-free synthesis (FIG. 23). However, the solvent-free protocol with conventional heating provided the most cost-efficient method with a cost to produce 1 kg of product as $3,895.97 (FIG. 23).

The relative comparison of both instruments demonstrates their applicability for synthesis of curcumin and curcumin analogs. The isolated yields comparison was affected by the purification procedure (FIG. 21, Table 9) due to difference in reaction volumes and solubility of products in corresponding solvents used. For experiments conducted using MARS 5 the extraction of the product was conducted using ethyl acetate/water system, while ethanol digestion was used for Biotage® Initator+.

In FIG. 22 we demonstrate summarized results obtained using EATOS software for conventional and microwave synthesis of curcumin with reagent prices acquired from Aldrich on May 20, 2021 according to the manufacturer site. $S^{-1}$ indicates the mass index per kg product. E indicates the environmental factor or waste generated per kg of product. EI_in and EI_out indicate the environmental indexes of the input and output substances. In FIG. 23, a cost analysis is performed on synthesis of 1 kg of curcumin using three different methodologies: 1) conventional heating solvent-based synthesis (on the left), 2) microwave-assisted solvent-free protocol (in the middle), and 3) solvent-free approach combined with conventional heating. The total cost to synthesize 1 kg of curcumin for $1^{st}$ protocol $6,455.78 (using literate yield 60%), for $2^{nd}$ method $4,876.10 (using 37% yield), and for the $3^{rd}$ approach $3,895.97 (using 72% estimated yield).

In FIG. 23 we used the same software to analyze the cost of production for conventional method using ethyl acetate as a solvent and conventional heating, while the microwave method used solvent-free conditions and microwave heating. Voltage and power usage of each microwave reactor were not included into the cost analysis. All of the cost comparison is based on our solvent-free method using Biotage single-mode reactor to allow one reaction to one reaction comparison.

In Table 9 comparison of two instruments using vanillin, p-anisaldehyde and p-chlorobenzaldehyde as starting materials is summarized. The use of vanillin provides curcumin as a final product, while other two aldehydes result in curcuminoids. We chose p-anisaldehyde to include a liquid starting material, and p-chlorobenzaldehyde as a solid starting material to allow analysis of how physical state impacts solvent-free method.

TABLE 9

Comparison of product yield.

| | Isolated Product Yield, % | |
|---|---|---|
| Starting Aldehyde Used | Biotage ® Iniator + EtOH workup* | MARS 5 EtOAc/$H_2O$ workup |
| p-anisaldehyde | 47.3 | 82.1 |
| p-chlorobenzaldehyde | 24.7 | 75.2 |
| vanillin | 37.2 | 72.3 |

*Based on spectroscopic analysis of remaining filtrates and quantitative integration of C(O)—H signal of an aldehyde and the trans-coupling signals of corresponding product we estimate the actual yield to be as high by 30-40%.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a compound having the structure:

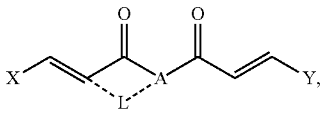

wherein

A is —C—,

X and Y are independently chosen from substituted or unsubstituted aryl, and substituted or unsubstituted heteroaryl, L is absent or is a substituted or unsubstituted linker group chosen from —$(CH_2)_3$—, —$(CH_2)_2$—, and —$CH_2$—$CH_2$—C(O)—.

Embodiment 2 provides the compound of Embodiment 1, wherein the compound is a curcuminoid.

Embodiment 3 provides the compound of any one of Embodiment 1, wherein the compound is an analog of a curcuminoid.

Embodiment 4 provides the compound of any one of Embodiments 1-3, wherein L is absent.

Embodiment 5 provides the compound of any one of Embodiments 1-4, wherein L is —$(CH_2)_3$—.

Embodiment 6 provides the compound of any one of Embodiments 1-5, wherein L is —$(CH_2)_2$—.

Embodiment 7 provides the compound of any one of Embodiments 1-6, wherein L is —$CH_2$—$CH_2$—C(O)—.

Embodiment 8 provides the compound of any one of Embodiments 1-7, wherein X and Y have the same structure.

Embodiment 9 provides the compound of any one of Embodiments 1-8, wherein X and Y have different structures.

Embodiment 10 provides the compound of any one of Embodiments 1-9, wherein X and Y are independently chosen from phenyl, 2-nitrophenyl, 3-nitrophenyl, 4-nitrophenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-hydroxyphenyl, 3-hydroxyphenyl, 4-hydroxyphenyl, 3,5-dimethoxyphenyl, 4-(trifluoromethyl)phenyl, 2-naphthyl, 6-methoxy-2-naphthyl, 3-methoxy-4-hydroxyphenyl, 2-hydroxy-3-methoxyphenyl, 4-cyanophenyl,

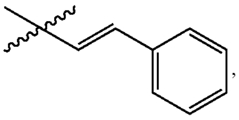,
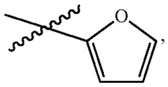,
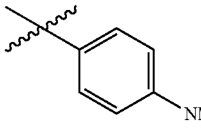,
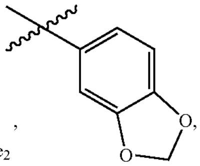, and
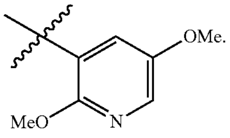

Embodiment 11 provides the compound of any one of Embodiments 1-10, wherein X and Y independently have the structure:

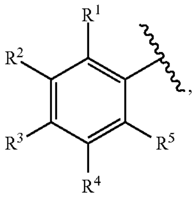, wherein $R^1$, $R^2$, $R^3$, $R^4$, and $R^5$ are independently chosen from —H, —$OCH_3$, —Cl, —Br, —F, —I, —CN, —$NO_2$, —$CF_3$, and —$N(CH_3)_2$.

Embodiment 12 provides the compound of any one of Embodiments 1-11, wherein the compound has the structure:

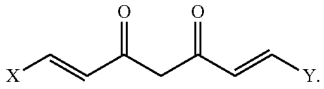

Embodiment 13 provides the compound of any one of Embodiments 1-12, wherein the compound has the structure:

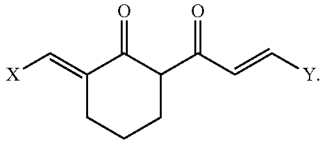

Embodiment 14 provides the compound of any one of Embodiments 1-13, wherein the compound has the structure:

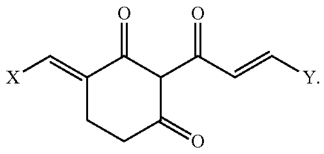

Embodiment 15 provides the compound of any one of Embodiments 1-14, wherein the compound has the structure:

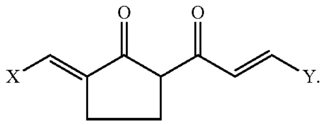

Embodiment 16 provides a method of making the compound of any one of Embodiments 1-15, the method comprising:

combining (e.g., combining and reacting)

acetylacetone, 2-acetylcylohexanone, 2-acetylcyclopentanone, or 2-acetylcyclohexane-1,3-dione, an aldehyde having the structure X—C(O)H and/or Y—C(O)H, $B_2O_3$, $R^B$— $N_2$, and $(R^BO)_3B$, to form the compound of any one of Embodiments 1-18;

wherein $R^B$ is independently $(C_1$-$C_{10})$alkyl.

Embodiment 17 provides the method of Embodiment 16, wherein $R^B$ is n-butyl.

Embodiment 18 provides the method of any one of Embodiments 16-17, wherein $R^B$ is isopropyl.

Embodiment 19 provides the method of any one of Embodiments 16-18, wherein the combining is performed in the absence of any added solvent.

Embodiment 20 provides the method of any one of Embodiments 16-19, wherein the one or more aldehydes are in a liquid state during the combining.

Embodiment 21 provides the method of any one of Embodiments 16-20, wherein the combining is performed with heating to 10-150° C.

Embodiment 22 provides the method of any one of Embodiments 16-21, wherein the combining is performed with heating to 40-100° C.

Embodiment 23 provides the method of any one of Embodiments 16-22, wherein the combining is performed with heating provided by microwave energy.

Embodiment 24 provides the method of any one of Embodiments 16-23, wherein the combining is performed for 1 h to 5 d.

Embodiment 25 provides the method of any one of Embodiments 16-24, wherein the combining is performed for 10 h to 24 h.

Embodiment 26 provides a method of treating a disease, comprising:

administering the compound of any one of Embodiments 1-15 to a subject that has the disease.

Embodiment 27 provides a method of killing a microbe or decreasing the rate of proliferation of a microbe, the method comprising:

contacting the microbe and the compound of any one of Embodiments 1-15.

Embodiment 28 provides the compound or method of any one or any combination of Embodiments 1-27 optionally configured such that all elements or options recited are available to use or select from.

What is claimed is:

1. A compound having the structure:

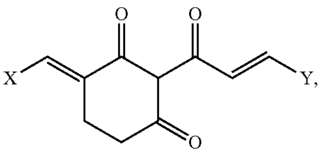

or

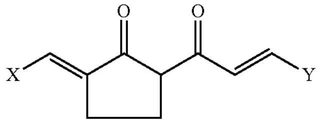

wherein

X and Y are independently chosen from substituted or unsubstituted aryl, and substituted or unsubstituted heteroaryl; and wherein X and Y have different structures, or X and Y are independently chosen from 2- nitrophenyl, 3-nitrophenyl, 4-nitrophenyl, 2-cholorophenyl, 3-cholorophenyl, 4-cholorophenyl, 2-fluorophenyl, 3-fluorophenyl, 4-fluorophenyl, 2-methoxyphenyl, 3-methoxyphenyl, 4-methoxyphenyl, 2-hydroxyphenyl, 3-hydroxyphenyl, 4-hydroxyphenyl, 3,5-dimethoxyphenyl, 4-(trifluoromethyl)phenyl, 2-naphthyl, 6-methoxy-2-naphthyl, 3-methoxy-4hydroxyphenyl, 2-hydroxy-3-methoxyphenyl, 4- cyanophenyl,

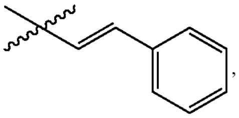

,

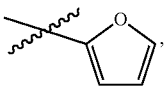

,

-continued

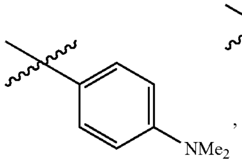

,

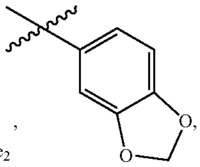

and

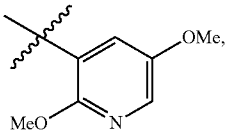

or the compound has the structure:

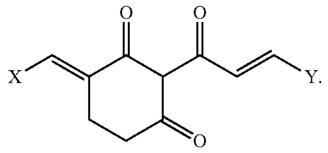

2. The compound of claim 1, wherein the compound is an analog of a curcuminoid.

3. The compound of claim 1, wherein X and Y have the same structure.

4. The compound of claim 1, wherein X and Y have different structures.

5. The compound of claim 1, wherein X and Y are independently chosen from 2-nitrophenyl, 3-nitrophenyl, 4-nitrophenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-hydroxyphenyl, 3-hydroxyphenyl, 4-hydroxyphenyl, 3,5-dimethoxyphenyl, 4-(trifluoromethyl) phenyl, 2-naphthyl, 6-methoxy-2-naphthyl, 3-methoxy-4-hydroxyphenyl, 2-hydroxy-3-methoxyphenyl, 4-cyanophenyl,

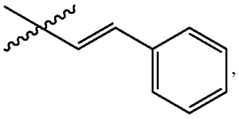

,

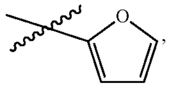

,

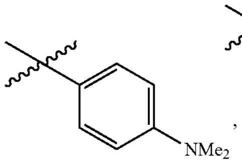

,

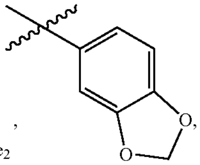

and

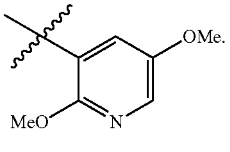

6. The compound of claim 1, wherein X and Y independently have the structure:

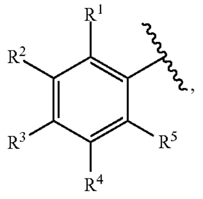

wherein $R^1$, $R^2$, $R^3$, $R^4$, and $R^5$ are independently chosen from —H, —$OCH_3$, —Cl, —Br, —F, —I, —CN, —$NO_2$, —$CF_3$, and —$N(CH_3)_2$.

7. The compound of claim 1, wherein the compound has the structure:

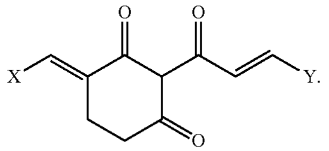

8. The compound of claim 1, wherein the compound has the structure:

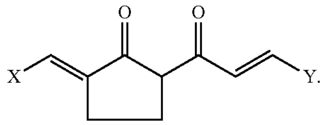

9. A method of making the compound of claim 1, the method comprising:

combining 2-acetylcylohexanone, 2-acetylcyclopentanone, or 2-acetylcyclohexane-1,3-dione, an aldehyde having the structure X—C(O)H and/or Y—C(O)H, $B_2O_3$, $R^B$—$NH_2$, and $(R^BO)_3B$, to form the compound of claim 1;

wherein $R^B$ is independently $(C_1\text{-}C_{10})$alkyl.

10. The method of claim 9, wherein $R^B$ is n-butyl or isopropyl.

11. The method of claim 9, wherein the combining is performed in the absence of any added solvent.

12. The method of claim 9, wherein the combining is performed with heating to 40-100° C.

13. The method of claim 9, wherein the combining is performed with heating provided by microwave energy.

14. A method of treating a disease, comprising:

administering the compound of claim 1 to a subject that has the disease.

15. A method of making a compound, the method comprising:

combining acetylacetone, 2-acetylcylohexanone, 2-acetylcyclopentanone, or 2-acetylcyclohexane-1,3-dione, an aldehyde having the structure X—C(O)H and/or Y—C(O)H, $B_2O_3$, $R^B$—$NH_2$, and $(R^BO)_3B$, wherein $R^B$ is independently $(C_1\text{-}C_{10})$ alkyl, to form the compound, wherein the compound has the structure:

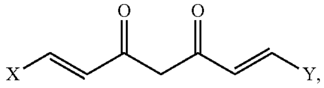

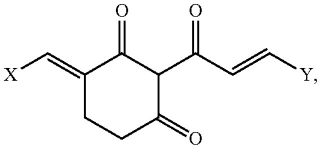

or

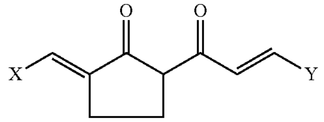

wherein

A is —C—,

X and Y are independently chosen from substituted or unsubstituted aryl, and substituted or unsubstituted heteroaryl; and wherein X and Y have different structures, or X and Y are independently chosen from 2- nitrophenyl, 3-nitrophenyl, 4-nitrophenyl, 2-cholorophenyl, 3-cholorophenyl, 4-cholorophenyl, 2-fluorophenyl, 3-fluorophenyl, 4-fluorophenyl, 2-methoxyphenyl, 3-methoxyphenyl, 4-methoxyphenyl, 2-hydroxyphenyl, 3-hydroxyphenyl, 4-hydroxyphenyl, 3,5-dimethoxyphenyl, 4-(trifluoromethyl)phenyl, 2-naphthyl, 6-methoxy-2-naphthyl, 3-methoxy-4hydroxyphenyl, 2-hydroxy-3-methoxyphenyl, 4- cyanophenyl,

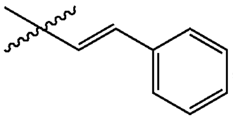,

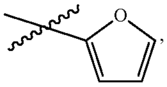,

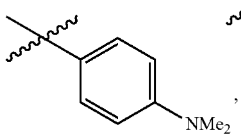,

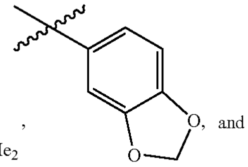, and

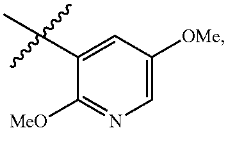, or the compound has the structure:

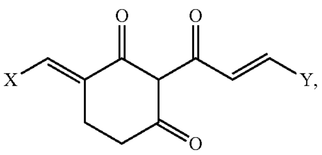

or

-continued

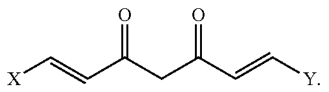

16. The method of claim 15, wherein X and Y are independently chosen from 2-nitrophenyl, 3-nitrophenyl, 4-nitrophenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-hydroxyphenyl, 3-hydroxyphenyl, 4-hydroxyphenyl, 3,5-dimethoxyphenyl, 4-(trifluoromethyl) phenyl, 2-naphthyl, 6-methoxy-2-naphthyl, 3-methoxy-4-hydroxyphenyl, 2-hydroxy-3-methoxyphenyl, 4-cyanophenyl,

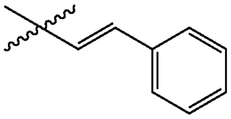, 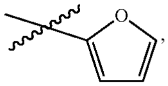,

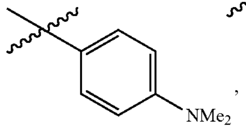, 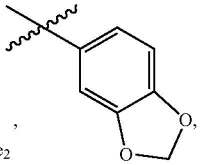, and

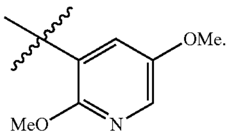

17. A compound having the structure:

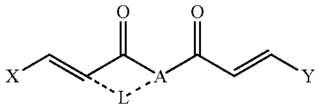

wherein

A is —C—,

X and Y are independently chosen from substituted or unsubstituted aryl, and substituted or unsubstituted heteroaryl, wherein X and Y have different structures, and L is a substituted or unsubstituted linker group chosen form —$(CH_2)_3$, —$(CH_2)_2$—, and —$CH_2$—$CH_2$—C(O)—.

18. A method of killing a microbe or decreasing the rate of proliferation of a microbe, the method comprising:

contacting the microbe and a compound having the structure:

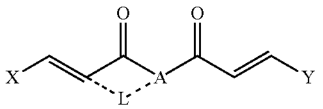

wherein

A is —C—,

X and Y are independently chosen from substituted or unsubstituted aryl, and substituted or unsubstituted heteroaryl, and L is a substituted or unsubstituted linker group chosen from —$(CH_2)_3$—, —$(CH_2)_2$—, and —$CH_2$—$CH_2$—C(O)—.

* * * * *